(12) United States Patent
Bergnes et al.

(10) Patent No.: US 7,211,580 B2
(45) Date of Patent: May 1, 2007

(54) COMPOUNDS, COMPOSITIONS, AND METHODS

(75) Inventors: Gustave Bergnes, Pacifica, CA (US); Whitney W. Smith, El Cerrito, CA (US); Bing Yao, Hayward, CA (US); David J. Morgans, Jr., Los Altos, CA (US); Andrew MacDonald, Mill Valley, CA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 421 days.

(21) Appl. No.: 10/626,012

(22) Filed: Jul. 23, 2003

(65) Prior Publication Data

US 2004/0142949 A1 Jul. 22, 2004

Related U.S. Application Data

(60) Provisional application No. 60/398,224, filed on Jul. 23, 2002.

(51) Int. Cl.
*A61K 31/517* (2006.01)
*C07D 401/00* (2006.01)
*C07D 239/72* (2006.01)

(52) U.S. Cl. .............................. 514/266.22; 514/266.2; 544/284; 544/287

(58) Field of Classification Search ............. 514/266.2, 514/266.22; 544/284, 287
See application file for complete search history.

(56) References Cited

U.S. PATENT DOCUMENTS

| | | | |
|---|---|---|---|
| 3,320,124 A | 5/1967 | Waletzky et al. |
| 3,322,756 A | 5/1967 | Ruschig et al. |
| 3,723,432 A | 3/1973 | Ott et al. |
| 3,740,442 A | 6/1973 | Ott et al. |
| 3,925,548 A | 12/1975 | Oh |
| 3,962,244 A | 6/1976 | Weyer et al. |
| 4,011,324 A | 3/1977 | Althuis |
| 4,281,127 A | 7/1981 | LaMahieu et al. |
| 4,729,996 A | 3/1988 | Wright et al. |
| 4,734,419 A | 3/1988 | Hashimoto et al. |
| 4,808,590 A | 2/1989 | Higa et al. |
| 4,857,530 A | 8/1989 | Berman et al. |
| 4,859,670 A | 8/1989 | Kampe et al. |
| 4,866,084 A | 9/1989 | Gunasekera et al. |
| 4,970,226 A | 11/1990 | Sun et al. |
| 4,981,856 A | 1/1991 | Hughes |
| 4,992,550 A | 2/1991 | Hughes |
| 5,037,829 A | 8/1991 | Freyne et al. |
| 5,081,124 A | 1/1992 | Hughes |
| 5,147,875 A | 9/1992 | Coates |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haughland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |
| 5,773,476 A | 6/1998 | Chen et al. |
| 5,777,115 A | 7/1998 | Leigh et al. |
| 5,780,476 A | 7/1998 | Underiner |
| 5,783,577 A | 7/1998 | Houghten et al. |
| 5,789,427 A | 8/1998 | Chen et al. |
| 5,795,898 A | 8/1998 | Brown et al. |
| 5,801,181 A | 9/1998 | Michnick et al. |
| 5,801,182 A | 9/1998 | Klein et al. |

(Continued)

FOREIGN PATENT DOCUMENTS

AU     B-12617/88     9/1988

(Continued)

OTHER PUBLICATIONS

Chemcats Copyright 2000 ACS, 1998:596123 CHEMCATS, Maybridge, Apr. 3, 2000, DP 01489, "N2-(3-pyridylmethyl)-4-oxo-3,4-dihydroquinazoline-2-carboxamide," 190437-46-8, Chemical Library.

(Continued)

*Primary Examiner*—James O. Wilson
*Assistant Examiner*—Tamthom N. Truong
(74) *Attorney, Agent, or Firm*—Finnegan, Henderson, Farabow, Garrett & Dunner, LLP

(57) ABSTRACT

Compounds, compositions and methods useful for treating cellular proliferative diseases and disorders, for example, by modulating the activity of KSP, are disclosed.

9 Claims, No Drawings

U.S. PATENT DOCUMENTS

| | | |
|---|---|---|
| 5,804,584 A | 9/1998 | Underiner et al. |
| 5,807,861 A | 9/1998 | Klein et al. |
| 5,807,862 A | 9/1998 | Klein et al. |
| 5,811,429 A | 9/1998 | Connell et al. |
| 5,817,662 A | 10/1998 | Klein et al. |
| 5,837,703 A | 11/1998 | Kumar et al. |
| 5,852,024 A | 12/1998 | Pines et al. |
| 5,859,018 A | 1/1999 | Brown et al. |
| 5,869,665 A | 2/1999 | Padia |
| 5,885,996 A | 3/1999 | Webber et al. |
| 5,891,879 A | 4/1999 | Nagler et al. |
| 5,892,114 A | 4/1999 | Goldmann et al. |
| 5,922,866 A | 7/1999 | Miyata et al. |
| 5,929,081 A | 7/1999 | Brown et al. |
| 5,939,421 A | 8/1999 | Palanki et al. |
| 5,948,775 A | 9/1999 | Koko et al. |
| 5,948,784 A | 9/1999 | Fujiwara et al. |
| 6,008,010 A | 12/1999 | Greenberger et al. |
| 6,136,812 A | 10/2000 | Chenard et al. |
| 6,156,758 A | 12/2000 | Kung et al. |
| 6,207,403 B1 | 3/2001 | Goldstein et al. |
| 6,245,768 B1 | 6/2001 | He et al. |
| 6,303,615 B1 * | 10/2001 | Elliott et al. ............. 514/266.2 |
| 6,545,004 B1 | 4/2003 | Finer et al. |
| 6,545,005 B1 | 4/2003 | Baxter et al. |
| 6,559,160 B1 | 5/2003 | Schall et al. |
| 6,562,831 B1 | 5/2003 | Finer et al. |
| 6,613,798 B1 | 9/2003 | Porter et al. |
| 6,627,755 B1 * | 9/2003 | Chenard et al. ............ 544/284 |
| 6,630,479 B1 | 10/2003 | Finer et al. |
| 6,753,428 B2 | 6/2004 | Bergnes et al. |
| 6,794,379 B2 | 9/2004 | Medina et al. |
| 6,831,085 B1 | 12/2004 | Bergnes et al. |
| 7,060,705 B2 * | 6/2006 | Fraley et al. ............ 514/266.2 |
| 2001/0046997 A1 | 11/2001 | Abraham et al. |
| 2002/0032207 A1 | 3/2002 | Thompson et al. |
| 2002/0055519 A1 | 5/2002 | Thompson et al. |
| 2002/0165221 A1 | 11/2002 | Baxter et al. |
| 2002/0169159 A1 | 11/2002 | Medina et al. |
| 2002/0198326 A1 * | 12/2002 | Aoyama et al. ............ 525/240 |
| 2003/0018038 A1 | 1/2003 | Thompson et al. |
| 2003/0055054 A1 | 3/2003 | Medina et al. |
| 2003/0091946 A1 | 5/2003 | Uchira et al. |
| 2003/0119834 A1 | 6/2003 | Bamdad |
| 2003/0130293 A1 | 7/2003 | Bamdad |
| 2003/0139398 A1 | 7/2003 | Hoekstra et al. |
| 2003/0139457 A1 * | 7/2003 | Baxter et al. ............... 514/357 |
| 2003/0144350 A1 | 7/2003 | Stevenson et al. |
| 2003/0158188 A1 | 8/2003 | Lee et al. |
| 2003/0158198 A1 | 8/2003 | Lee et al. |
| 2003/0166933 A1 | 9/2003 | Bergnes et al. |
| 2003/0171387 A1 | 9/2003 | Sun et al. |
| 2003/0195211 A1 | 10/2003 | Sadhu et al. |
| 2003/0220338 A1 | 11/2003 | Watkins et al. |
| 2003/0220356 A1 | 11/2003 | Ibrahim et al. |
| 2004/0023996 A1 | 2/2004 | Finer et al. |
| 2004/0048853 A1 | 3/2004 | Bergnes |
| 2004/0067969 A1 | 4/2004 | Bergnes et al. |
| 2004/0077662 A1 | 4/2004 | Zhou et al. |
| 2004/0077667 A1 | 4/2004 | Matsuoka et al. |
| 2004/0077668 A1 | 4/2004 | Feng et al. |
| 2004/0082567 A1 | 4/2004 | McDonald et al. |
| 2004/0092561 A1 | 5/2004 | Ruckle et al. |
| 2004/0116438 A1 | 6/2004 | Lu et al. |
| 2004/0142949 A1 | 7/2004 | Bergnes et al. |
| 2004/0192913 A1 | 9/2004 | Bergnes et al. |
| 2004/0242596 A1 | 12/2004 | Kim et al. |
| 2004/0259826 A1 | 12/2004 | Fraley et al. |
| 2005/0152940 A1 | 7/2005 | Hezi-Yamit et al. |
| 2005/0209254 A1 | 9/2005 | Wang et al. |

FOREIGN PATENT DOCUMENTS

| | | |
|---|---|---|
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 509 643 A1 | 10/1992 |
| EP | 0 512 676 A1 | 11/1992 |
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| JP | 10/259176 | 9/1998 |
| WO | WO 91/12001 A1 | 8/1991 |
| WO | WO 93/11115 A2 | 6/1993 |
| WO | WO 93/19051 A1 | 9/1993 |
| WO | WO 93/20055 A1 | 10/1993 |
| WO | WO 93/23404 A1 | 11/1993 |
| WO | WO 94/21259 A1 | 9/1994 |
| WO | WO 95/16682 A1 | 6/1995 |
| WO | WO 95/19169 A2 | 7/1995 |
| WO | WO 95/24379 A1 | 9/1995 |
| WO | WO 96/06616 A1 | 3/1996 |
| WO | WO 96/19224 A1 | 6/1996 |
| WO | WO 96/28430 A1 | 9/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 99/20298 A1 | 4/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |
| WO | WO 01/66519 A2 | 9/2001 |
| WO | WO 01/70737 A2 | 9/2001 |
| WO | WO 01/81346 A2 | 11/2001 |
| WO | WO 01/95884 A2 | 12/2001 |
| WO | WO 01/98278 A1 | 12/2001 |
| WO | WO 02/04444 A2 | 1/2002 |
| WO | WO 02/08224 A1 | 1/2002 |

| | | |
|---|---|---|
| WO | WO 02/09713 A2 | 2/2002 |
| WO | WO 02/09713 A3 | 2/2002 |
| WO | WO 02/14319 A2 | 2/2002 |
| WO | WO 02/30462 A2 | 4/2002 |
| WO | WO 02/083143 A1 | 10/2002 |
| WO | WO 02/094790 A1 | 11/2002 |
| WO | WO 03/020279 A2 | 3/2003 |
| WO | WO 03/020280 A2 | 3/2003 |
| WO | WO 03/027234 A2 | 4/2003 |
| WO | WO 03/035076 A1 | 5/2003 |
| WO | WO 03/035077 A1 | 5/2003 |
| WO | WO 03/039460 A2 | 5/2003 |
| WO | WO 03/043961 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |
| WO | WO 03/079973 A2 | 10/2003 |
| WO | WO 03/084544 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A1 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

Q. Kozhevnikov et al. 4-Quinazolinones. II. 2-(Aminomethyl)-3-aryl-4-quinazolinones. (Russian) Tr Perm Sel-Khoz Inst. 79: 66-72 (1971). Chem Abstracts 78: 390 (1973).
Gupta, C.M. et al. "Drugs acting on the central nervous system. Synthesis of substituted quinazolones and quinazolines and triazepino- and triazocinoquinazolones," *J. Med. Chem.* 11: 392-395 (1968).
Saari, W.S. et al. "Synthesis and evaluation of 2-pyridinone derivatives as HIV-1-specific reverse transcriptase inhibitors. 2. Analogues of 3-aminopyridin-2(1H)-one," *J. Med. Chem.* 35: 3792-3802 (1992).
Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).
Dymek, W. et al. "2-Chloromethyl-6-methylquinazolone-4 and its transformations," *Diss. Pharm. Et Pharmacol.* 20(1): 29-34 (1968).
Pattanaik, J.M. et al. "Synthesis and fungicidal activity of 3-aryl-2-(4'-aryl thiazol-2'-ylaminomethyl) quinazol-4-(3H)-ones," *Indian J. Chem.* 37B: 1304-1306 (1998).
Gupta, D.P.,e t al. "Thiazolidinones, azetidinones and formazans of quinazolinones," *Indian J. Chem.* 26B: 1197-1199 (1987).
Parasharya, P.M. et al. "4 (3H)-Quinazolones. Part I: 2-Alkyl/arylaminomethyl-3-p-hyroxy/methoxyphenyl-4(3H)-quinazolones," J. Inst. Chemists (India) 64: 184-185 (1992).
Parasharya, P.M. et al. "4-(3H)-Quinazolones: 2-N-aryl/alkyl-amino-methyl/ethyl-3-p-hydroxyphenyl/p-anisyl/p-arylaminoacyloxyphenyl/p-N-arylcarbamoylmethoxyphenyl-4-(3H)-quinazolones," *J. Inst. Chemists* (India) 64: 238-241 (1992).
Matthews, N. et al. "Structure-activity relationships of phenothiazines in inhibiting lymphocyte motility as determined by a novel flow cytometric assay," *Biochem. Pharmacol.* 50(7): 1053-1061 (1995).
List of Purchased Compounds Oct. 2000.
Debnath, A.K. "Structure-Based Identification of Small Molecule Antiviral Compounds Targeted to the gp41 Core Structure of the Human Immunodeficiency Virus Type 1," *J. Med. Chem.* 42 (17): 3203-3209 (1999).
Bocskei, Z. et al.. "Two Antithrombotic Quinazolone Derivatives." *Acta Crystallogr., Sect. C: Cryst. Struct. Commun.* C51(4): 723-726 (1995).
Szabo, M. et al. "Synthesis of Potential CCK Antagonist Quinazolone Derivatives," Chemical Abstracts, vol. 124, No. 13, Abstract No. 176002v (1995).
Ager et al. "Synthesis and Central Nervous System Activity of Quinazolones Related to 2-Methyl-3-(o-tolyl)-4(3H) quinazolone (Methaqualone)," *J. Med. Chem.* 20(3): 379-386 (1977).
Tiwari et al. "Synthesis and CNS Activity of 2-Aryl-3(3'-, 4'-Dihyroxyphenylethyl) 6-8-substituted-4 (3H)Quinazolinones," *Indian J. Pharm. Sci.* pp. 40-43 (1978).
Rao et al. "Synthesis and Biological Activities of Certain Derivatives of 3-Aryl-4(3h)-quinazolinones, Part-II," *J. Indian Chem. Soc.* LXII: 234-237 (1985).
Registry file compounds from unspecified chemical libraries.
Commercially available from ComGenex, Sep. 16, 1999.
Registry File Compounds from Published References, Maybridge Catalog, Apr. 3, 2000.
Singh et al. Chemical Abstracts, vol. 92, Abstract No. 58712 (1980).
Spirkova et al., Chemical Abstracts, vol. 132, Abstract No. 35672 (1999).
Pandey et al. Chemical Abstracts, vol. 124, Abstract No. 331723 (1996).
Parasharya et al. Chemical Abstracts, vol. 121, Abstract No. 108675 (1994).
Saari et al. Chemical Abstracts, vol. 117, Abstract No. 191731 (1992).
Farghaly et al. Chemical Abstracts, vol. 114, Abstract No. 122242 (1991).
El-Nasser Ossman et al. Chemical Abstracts, vol. 106, Abstract No. 207516 (1987).
Rao et al. Chemical Abstracts, vol. 105, Abstract No. 97416 (1986).
Gupta et al. Chemical Abstracts, vol. 69, Abstract No. 42637 (1968).
Kumar et al. Chemical Abstracts, vol. 102, Abstract No. 142800 (1985).
Chaurasia et al. Chemical Abstracts, vol. 96, Abstract No. 6681 (1982).
Tani et al. Chemical Abstracts, vol. 93, Abstract No. 26374 (1980).
Ager et al. Chemical Abstracts, vol. 86, Abstract No. 83505 (1977).
Kozhevnikov et al. Chemical Abstracts, vol. 78, Abstract No. 16128U (1971).
Bergman et al. "Synthesis of Chrysogine, a Metabolite of *Penicillium chrysogenum* and some related 2-substituted 4-(3H)-Quinazolinones," *Tetrahedron* 46: 1295-1310 (1990).
Hart et al. "Synthesis of (-)-Alantrypinone," *Tet. Lett.* 40: 5429-5432 (1999).
Hart et al. "Synthesis of *ent*-Alantrypinone" *J. Am. Chem. Soc.* 123: 5892-5899 (2001).
Mayer et al. "Solid phase synthesis of quinazolinones" *Tet. Lett.* 38(49):8445-8448 (1997).
Prashad et al. "Reaction of benzoyleneurea and isatoic anhydride with the Vilsmeier reagent" *Tet. Lett.* 38(8):1313-1316 (1997).
Villalgordo et al. "Solid-phase synthesis of 3H-quinazolin-4-ones based on an aza Wittig-mediated annulation strategy" *Synlett* 1405-1407 (1998).
Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." *Synlett* 7:1100-1102 (1999).

Wang et al. "Total synthesis of the quinazolinone alkaloids (-)-Fumiquinazoline G and (-)-Fiscalin B" *J. Org. Chem.* 63:2432-2433 (1998).

Padia et al. "Novel nonpeptide CCK-B antagonists: Design and development of quinazolinone derivatives as potent, selective, and orally active CCK-B antagonists" *J. Med. Chem.* 41:1042-1049 (1998).

Singh et al. "4-Quinazolones—II Synthesis of some imidazo [1,5-a] quinazolones" *J. Indian Chem. Soc.* 46(1):21-25 (1969).

Badawy et al. "Chemistry of Quinazolines: Reinvestigation of the Action of Hydrazine on Thioxo Derivatives" *J. Heterocyclic Chem.* 22: 1535-1536 (1985).

Yu et al. "Synthesis and x-ray crystallographic analysis of quinazolinone cholecystokinin/gastrin receptor ligands" *J. Med. Chem.* 35:2534-2542 (1992).

Zaher et al. "Reactions of 2-p-anisyl-3(4H), 1-benzoxazin-4-one with ammonia, primary amines, hydrazine, phenylhydrazine & Grignard reagents" *Indian J. Chem.* 12:1212-1215 (1974).

Kulkami et al. "Possible antifertility agents. Part-I. Synthesis of 2-(N,N-substituted-aminomethyl)-3-(2-pyridyl)-4(3H)-oxo-3,1-quinazolines" *J. Indian Chem.* LXI:720-721 (1984).

Majo et al. "Dimerization of substituted 2-aminobenzoic acids under Vilsmeier conditions: A novel route to the synthesis of 4-(3H)-quinazolinones" *Tet. Lett.* 37(28):5015-5018 (1996).

Rathman et al. "Functionalization of 2-methyl-3-o-tolyl-4(3H)-quinazolinone and related compounds through carbanion reactions at the 2-methyl group" *J. Org. Chem.* 45:2169-2176 (1980).

Padia et al. "Design and synthesis of novel nonpeptide CCK-B receptor antagonists" *Bioorg. Med. Chem. Lett.* 7(7):805-810 (1997).

Zentmyer et al. "The so-called acylanthranils (3,1,4-benzoxazones). I. Prepation; reactions with water, ammonia, and aniline; structure" *J. Organic Chemistry*, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" *Acta Ciencia Indica* 4(3):230-235 (1978).

Tiwari et al. Chemical Abstracts, vol. 96, Abstract No. 142790p (1982).

Fadda et al. "Reactions of a heterocyclic β-enaminoester: Synthesis of pyranopyrimidines and pyrano[3', 2', : 5,6]pyrimidino[2,3-c][1,4]benzoxazine ring system," *Indian J. Chemistry* 29B: 1020-1024 (1990).

Wagner "Synthesis and Biological Evaluation of Some Derivatives of Pyrido[3, 2-d]pyrimidine" *Acta Poloniae Pharmaceutica—Drug Research* 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" *J. Chem Research (S)*: 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether" *J. Med. Chem* 44:1710-1717 (2001).

Garg et al. "Synthesis and anti-implantation activity of α-(2-aryl-3-ethyl-4-oxo (3H) quinazolinyl)-α-(substituted styryl)-cyclohexanone thiosemicarbazones" *Biol. Mem.* 14(2):180-186 (1988).

Singh et al. "Synthesis and pharmacological screening of some 2-aryl-3-(phenyl-aryl-hydrazonyl)-quinazolin (3H) 4-ones" *Indian Drugs* 28(2):70-74 (1990).

Ahmad et al. "Monoamine oxidase Inhibitory Activity of 4 (3H)-Quinazolinones of Dopamine" *Indian J. of Pharm. Sci.* 126-127 (1979).

Tiwari et al. "Possible Antifertility Compounds Part III: Synthesis of 2-Hippuryl-3-Aryl-Quinazolinones" *J. Chem. Soc. Pak.* 3(4):215-217 (1981).

Pandey, V.K. "Antiparkinsonism and CNS Activities of 2-aryl alkyl-3-[β-(3'-4'-dihydroxyphenyl) Ethyl]-quinazolin (3H) 4-ones" *Biol. Mem.* 11(2):213-215 (1985).

Monika et al. "Uj kinazolonszarmazekok szintezise es ciklizalasa [1,4]oxazepino- es [1,4]diazepino [3,4-b]kinazolonkka" *Magyar Kemiai Folyoirat* 102(8):343-355 (1996) translated abstract.

Reddy et al. "A New Synthesis of 2-aryl-2H-Pyrazino[2,1-β]Quinazolin-3,6(1H,4H)-Diones" *Synthetic Communications* 21(2):173-181 (1991).

Monika et al. "Potencialis CCK-antagonista kinazolon-szarmazekok szintezse" *Acta Pharm. Hungarica* 65:133-136 (1995) translated abstract.

Pandey et al. "Quinazolyl-thiazoles as CNS acting agents" *Acta Pharm.* 46:51-59 (1996).

Reddy et al. "4-Heteryl-β-lactams: A facile synthesis of 1-aryl-4-[isopropylideneamino/methyl-4(3H)-oxoquinazolin-2-yl] azetidin-2-ones" *Indian J. of Chem.* 38B:40-44 (1999).

Reddy et al. "Bisazaheterocycles: Part VII—Synthesis of novel bisquinazolinonyl β-lactams" *Ind. J. of Chem.* 41B:1946-1949 (2002).

Krisztina et al. "Az AGP-alapu folyadek-kromatografias allofazis alkalmazasa kinazolon szarmazekok enantiomerjeinek elvalasztasaban" *Acta Pharma. Hungarica* 73:5-12 (2003) translated abstract.

Reddy et al. "Synthesis of 2-quinazolinonyl imidazolidinones" *Ind. J. of Chem.* 42B:393-396 (2003).

Gyimesi-Forras et al. "Optical Resolution of a Series of Potential Cholecystokinin Antagonist 4(3H)-Quinazolone Derivatives by Chiral Liquid Chromatography on $\alpha_1$-Acid Glycoprotein Stationary Phase" *J. of Chromat. Sci.* 38:430-434 (2000).

Jiang et al. "A Salt Bridge between an N-terminal Coiled Coil of gp41 and an Antiviral Agent Targeted to the gp41 Core Is Important for Anti-HIV-1 Activity" *Biochem. and Biophys. Res. Communications* 270:153-157 (2000).

Hughes et al. "Quinazoline Antifolate Thymidylate Synthase Inhibitors: Alkyl, Substituted Alkyl, and Aryl Substituents in the C2 Position" *J. Med. Chem.* 33:3060-3067 (1990).

Hassanein et al. "Sythesis of 2-substituted-10H-[1,2,4] triazino [6,1-b] quinazoline-10-ones and 8,13,14,16 tetrahydronaphtho [2',3',:3,4] [1,2,5] triazepino [7,1-b] quinazoline-8,13,16-triones with biological interest" *Al-Azhar Bull. Sci.* 8(2):417-434 (1997).

Szabo et al. "Nitrogen Bridgehead Compounds: Part 88 [1], Synthesis of 3H,7H-[1,4]Diazepino[3,4-b]quinazoline-3,7-diones" *J. Heterocyclic Chem.* 34(21):21-25 (1997).

Kokosi et al. "Nitrogen Bridgehead Compounds Part 90. An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).

El-Maghraby et al. "Synthesis of Glycylaminothiazoles" *Ind. J. Chem.* 12:1058-1059 (1974).

Hassan et al. "Synthesis and antimicrobial activity of some new N-aminoacyl derivatives of 2-amino-4-phenylthiazole" *Acta Pharm.* 47:159-166 (1997).

West, "Solid State Chemistry and it's Applications," Wiley, New York, 1988, pp. 358 & 365.

Office Action mailed May 7, 2001, for U.S. Appl. No. 09/699,047, filed Oct. 24, 2000.

Office Action mailed Apr. 24, 2002, for U.S. Appl. No. 09/699,047, filed Oct. 24, 2000.

Office Action mailed Feb. 6, 2002, for U.S. Appl. No. 09/724,644, filed Nov. 28, 2000.

Office Action mailed Oct. 21, 2002, for U.S. Appl. No. 09/724,644, filed Nov. 28, 2000.

Office Action mailed Feb. 6, 2002, for U.S. Appl. No. 09/724,712, filed Nov. 28, 2000.

Office Action mailed Apr. 9, 2002, for U.S. Appl. No. 09/724,713, filed Nov. 28, 2000.

Office Action mailed Oct. 21, 2002, for U.S. Appl. No. 09/724,713, filed Nov. 28, 2000.

Office Action mailed Mar. 22, 2002, for U.S. Appl. No. 09/724,897, filed Nov. 28, 2000.

Office Action mailed Dec. 17, 2002, for U.S. Appl. No. 09/724,897, filed Nov. 28, 2000.

Office Action mailed Jul. 11, 2003, for U.S. Appl. No. 09/724,897, filed Nov. 28, 2000.

Office Action mailed May 12, 2004, for U.S. Appl. No. 09/724,897, filed Nov. 28, 2000.
Office Action mailed Jul. 26, 2002, for U.S. Appl. No. 09/724,941, filed Nov. 28, 2000.
Office Action mailed Jan. 13, 2003, for U.S. Appl. No. 09/724,941, filed Nov. 28, 2000.
Office Action mailed Jan. 7, 2004, for U.S. Appl. No. 09/724,941, filed Nov. 28, 2000.
Office Action mailed Jul. 3, 2002, for U.S. Appl. No. 09/724,778, filed Nov. 28, 2000.
Office Action mailed Dec. 27, 2002, for U.S. Appl. No. 09/724,778, filed Nov. 28, 2000.
Office Action mailed Aug. 8, 2003, for U.S. Appl. No. 09/724,778, filed Nov. 28, 2000.
Office Action mailed Dec. 29, 2003, for U.S. Appl. No. 09/724,778, filed Nov. 28, 2000.
Office Action mailed Mar. 30, 2004, for U.S. Appl. No. 09/724,778, filed Nov. 28, 2000.
Office Action mailed Jun. 25, 2004, for U.S. Appl. No. 09/724,778, filed Nov. 28, 2000.
International Search Report mailed Feb. 22, 2001, for PCT Application No. PCT/US00/29585, filed Oct. 26, 2000.
Written Opinion mailed Sep. 21, 2001, for PCT Application No. PCT/US00/29585, filed Oct. 26, 2000.
International Preliminary Examination Report mailed Jan. 17, 2002, for PCT Application No. PCT/US00/29585, filed Oct. 26, 2000.
Office Action mailed Aug. 8, 2003, for U.S. Appl. No. 10/300,967, filed Nov. 20, 2002.
International Search Report mailed Feb. 7, 2003, for PCT Application No. PCT/US02/37410, filed Nov. 20, 2002.
Written Opinion mailed Sep. 9, 2003, for PCT Application No. PCT/US02/37410, filed Nov. 20, 2002.
International Preliminary Examination Report mailed Aug. 11, 2004, for PCT Application No. PCT/US02/37410, filed Nov. 20, 2002.
International Search Report mailed Oct. 31, 2001, for PCT Application No. PCT/US01/13901, filed Apr. 27, 2001.
International Search Report mailed Oct. 17, 2003, for PCT Application No. PCT/US03/18778, filed Jun. 12, 2003.
Office Action mailed Oct. 18, 2004, for U.S. Appl. No. 10/462,002, filed Jun. 12, 2003.
Written Opinion mailed Mar. 2, 2004, for PCT Application No. PCT/US03/18778, filed Jun. 12, 2003.
International Preliminary Examination Report mailed Sep. 8, 2004, for PCT Application No. PCT/US03/18778, filed Jun. 12, 2003.
International Search Report and Written Opinion mailed Dec. 6, 2004, for PCT Application No. PCT/US04/01279, filed Jan. 20, 2004.
International Search Report mailed Aug. 29, 2003, for PCT Application No. PCT/US03/14787, filed May 9, 2003.
Written Opinion mailed Jun. 10, 2004, for PCT Application No. PCT/US03/14787, filed May 9, 2003.
International Preliminary Examination Report mailed Nov. 16, 2004, for PCT Application No. PCT/US03/14787, filed May 9, 2003.
International Search Report mailed Jul. 16, 2004, for PCT Application No. PCT/US03/13627, filed May 2, 2003.
Office Action mailed Nov. 2, 2004, for U.S. Appl. No. 10/366,828; filed Feb. 14, 2003.
International Search Report mailed Aug. 12, 2003, for PCT Application No. PCT/US03/04713, filed Feb. 14, 2003.
Written Opinion mailed Jun. 24, 2004, for PCT Application No. PCT/US03/04713, filed Feb. 14, 2003.
International Preliminary Examination Report mailed Dec. 8, 2004, for PCT Application No. PCT/US03/04713, filed Feb. 14, 2003.
International Search Report mailed Jul. 9, 2004, for PCT Application No. PCT/US03/23319, filed Jul. 23, 2003.
International Preliminary Examination Report mailed Sep. 30, 2004, for PCT Application No. PCT/US03/23319, filed Jul. 23, 2003.
International Search Report mailed May 20, 2004, for PCT Application No. PCT/US03/26093, filed Aug. 20, 2003.
International Preliminary Examination Report mailed Aug. 5, 2004, for PCT Application No. PCT/US03/26093, filed Aug. 20, 2003.
Office Action mailed Jan. 4, 2005, for U.S. Appl. No. 10/444,283, filed May 22, 2003.
International Search Report mailed Dec. 18, 2003, for PCT Application No. PCT/US03/16500, filed May 22, 2003.
International Preliminary Examination Report mailed Jun. 23, 2004, for PCT Application No. PCT/US03/16500, filed May 22, 2003.
Bergnes et al., "Compounds, Compositions, and Methods," U.S. Appl. No. 10/980,627, filed Nov. 2, 2004.
Bergnes et al., "Compounds, Compositions, and Methods," U.S. Appl. No. 10/982,195, filed Nov. 5, 2004.
Bergnes, "Compounds, Compositions, and Methods," U.S. Appl. No. 11/005,629, filed Dec. 7, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. App. No. 10/435,069, filed May 8, 2005.
International Preliminary Examination Report mailed Jan. 28, 2005, for PCT Application No. PCT/US03/30788, filed Sep. 30, 2003.
Office Action mailed Apr. 27, 2005, for U.S. Appl. No. 10/429,195, filed May 2, 2003.
International Preliminary Examination Report mailed May 9, 2005, for PCT Application No. PCT/US03/13627, filed May 2, 2003.
International Search Report and Written Opinion mailed Apr. 28, 2005, for PCT Application No. PCT/US04/362653, filed Nov. 2, 2004.
International Search Report and Written Opinion mailed Jun. 14, 2005, for PCT Application No. PCT/US04/36853, filed Nov. 5, 2004.
Sauter et al., CAPLUS Abstract No. 87:84931 (1977).
Uchida et al., CAPLUS Abstract No. 81:152142 (1974).
Yamada et al., CAPLUS Abstract No. 134:252363 (2001).
Matsuoka et al., CAPLUS Abstract No. 133:150920 (2000).
Nugent et al., CAPLUS Abstract No. 123:143921 (1995).
De Melo et al., CAPLUS Abstract No. 117:143023 (1992).
Irikura et al., CAPLUS Abstract No. 105:42834 (1986).
Kyorin Pharmaceutical Co., Ltd., CAPLUS Abstract No. 103:87901 (1985).
Shuto et al., CAPLUS Abstract No. 90:72134 (1979).
Katagiri et al., CAPLUS Abstract No. 100:51536 (1984).
Hegrand et al., CAPLUS Abstract No. 80:98573 (1974).
Witkop et al., CAPLUS Abstract No. 75:77191 (1971).
Office Action mailed Jun. 24, 2005, for U.S. Appl. No. 10/773,602, filed Feb. 6, 2004.
Office Action mailed Jul. 6, 2005, for U.S. Appl. No. 10/982,195, filed Nov. 5, 2004.
Gavezzotti "Are Crystal Structures Predictable" *Acc. Chem. Res.* 27:309-314 (1994).
Wolff (ed.) *Burger's Medicinal Chemistry and Drug Discovery*, 5th Edition vol. 1: *Principles and Practice*, John Wiley & Sons, New York, pp. 975-977 (1995).
Banker et al. (eds.) *Modern Pharmaceuticals Third Edition, Revised and Expanded*, Marcel Dekker, Inc., New York, pp. 451 & 596 (1996).
Coleman et al. "Inhibitors of the mitotic kinesin spindle protein" *Expert Opin. Ther. Patents* 14(12): 1659-1667 (2004).
Li et al. "Discovery and development of antimitotic agents that inhibit tubulin polymerisation for the treatment of cancer" *Expert Opin. Ther. Patents* 12(11): 1663-1702 (2002).
Malik et al., "Compositions, Devices and Methods for Treating Cardiovascular Disease," U.S. Appl. No. 11/147,406, filed Jun. 7, 2005.
International Search Report and Written Opinion mailed Oct. 21, 2005, for PCT Application No. PCT/US05/19791, filed Jun. 7, 2005.
Franco et al., "Functional association of retinoic acid and *hedgehog* signaling in *Xenopus* primary neurogenesis," *Development*, 126: 4257-4265 (1999).
Gaffield et al., "A Looking Glass Perspective: Thalidomide and Cyclopamine," *Cellular and Molecular Biology*, 45(5): 579-588 (1999).

Ghorab, "Synthesis of Some New Thiadizole, Selena, Triazine, Thiazole and Cyanopyridine Derivatives with Assay for Their Antitumor Activity," *Phosphorus, Sulfur, and Silicon*, 112: 7-17 (1996).

Gailani et al., "The role of the human homologue of *Drosophilia* patched in sporadic basal cell carcinomas," *Nature Genetics*, 14: 78-81 (1996).

Ghorab et al., "Synthesis and effect of some new [1,2,4]triazolo[4,3-a]quinazolin-5(4*H*)-ones and related compounds on Ehrlich Ascites Carcinoma cells," *Acta Pharm.*, 49: 1-10 (1999).

Jiang et al., "Synthesis and Biological Evaluation of 2-Styrylquinazolin-4(3*H*)-ones, a New Class of Antimitotic Anticancer Agents Which Inhibit Tubulin Polymerization," *J. Med. Chem.*, 33: 1721-1728 (1990).

Smith et al., "Effects of Gastrin, Proglumide, and Somatostatin on Growth of Human Colon Cancer," *Gastroenterology*, 95: 1541-1548 (1988).

"Signal Transduction," from the *Dictionary of Biology*, Penguin Books, Ninth Edition reprinted with minor revisions, pp. 574-575 (1995).

"Hyper-," from *The British Medical Dictionary*, Caxton, p. 706 (circa 1961).

"Inhibit," from *The British Medical Dictionary*, Caxton, p. 747 (circa 1961).

Ghosh, "Quinazolines. Part I.," *J. Indian Chemical Society*, XIV: 411-413 (1937).

Mayer et al, "Small Molecule Inhibitor of Mitotic Spindle Bipolarity Identified in a Phenotype-Based Screen," *Science*, 286: 971-974 (1999).

Tortora et al., "Oral Administration of a Novel Taxane, an Antisense Oligonucleotide Targeting Protein Kinase A, and the Epidermal Growth Factor Receptor Inhibitor Iressa Causes Cooperative Antitumor and Antiangiogenic Activity," *Clinical Cancer Research*, 7: 4156-4163 (2001).

Guo et al., "Overexpression of Bax Enhances Antitumor Activity of Chemotherapeutic Agents in Human Head and Neck Squamous Cell Carcinoma," *Clinical Cancer Research*, 6: 718-724 (2000).

Simone, "Oncology: Introduction," *Cecil Textbook of Medicine, $20^{th}$ Edition*, 1: 1004-1010 (1996).

Farrell et al., "The role of ATP hydrolysis for kinesin processivity," PubMed Abstract only, *J Biol Chem*, 277(19): 17079-17087 (2002).

Yildiz et al., "Kinesin: walking, crawling or sliding along?" *TRENDS in Cell Biology*, 15(2): 112-120 (2005).

Office Action mailed Dec. 5, 2005, for U.S. Appl. No. 10/429,195, filed May 2, 2003.

Office Action mailed Dec. 6, 2005, for U.S. Appl. No. 10/644,244, filed Aug. 20, 2003.

Office Action mailed Dec. 20, 2005, for U.S. Appl. No. 10/893,929, filed Jul. 20, 2004.

\* cited by examiner

COMPOUNDS, COMPOSITIONS, AND METHODS

CROSS-REFERENCE TO RELATED APPLICATIONS

This application claims the benefit of co-pending provisional U.S. application Ser. No. 60/398,224, filed Jul. 23, 2002 incorporated herein by reference.

FIELD OF THE INVENTION

This invention relates to quinazolinone-like derivatives that are inhibitors of the mitotic kinesin KSP and are useful in the treatment of cellular proliferative diseases, for example cancer, hyperplasias, restenosis, cardiac hypertrophy, immune disorders and inflammation.

BACKGROUND OF THE INVENTION

The mitotic spindle is responsible for distribution of replicate copies of the genome to each of the two daughter cells that result from cell division. Disruption of the mitotic spindle can inhibit cell division, and induce cell death. Microtubules are the primary structural element of the mitotic spindle; they are the site of action of certain existing therapeutic agents used to treat cancer, such as taxanes and vinca alkaloids. Microtubules, however, exist as elements in other types of cellular structures (including tracks for intracellular transport in nerve processes). The therapeutic targeting of microtubules can, therefore, modulate processes in addition to cellular proliferation, leading to side effects that limit the usefulness of such drugs.

Improvement in the specificity of agents used to treat cancer is of considerable interest because of the therapeutic benefits that would be realized if the side effects associated with the administration of these agents could be reduced. Dramatic improvements in the treatment of cancer have been associated with identification of therapeutic agents acting through novel mechanisms. Examples of this include not only the taxanes, but also the camptothecin class of topoisomerase I inhibitors.

One novel anti-proliferative mechanism entails selective inhibition of mitotic kinesins, enzymes that are essential for assembly and function of the mitotic spindle, but are not generally part of other microtubule structures, such as in nerve processes. See, e.g., Guidebook to the Cytoskeletal and Motor Proteins, Kreis and Vale, Eds., pp. 389–394 (Oxford University Press 1999). Mitotic kinesins play essential roles during all phases of mitosis. These enzymes are "molecular motors" that transform energy released by hydrolysis of ATP into mechanical force that drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death. Mitotic kinesins are attractive targets for the discovery and development of novel anti-mitotic chemotherapeutics.

Among the mitotic kinesins that have been identified is KSP. KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159–69 (1995); Whitehead, et al., Arthritis Rheum., 39:1635–42 (1996); Galgio et al., J. Cell Biol., 135:339–414 (1996); Blangy, et al., J Biol. Chem., 272:19418–24 (1997); Blangy, et al., Cell Motil. Cytoskeleton, 40:174–82 (1998); Whitehead and Rattner, J. Cell Sci., 111:2551–61 (1998); Kaiser, et al., JBC 274:18925–31 (1999); GenBank accession numbers: X85137, NM004523 and U37426], and a fragment of the KSP gene (TRIP5) has been described [Lee, et al., Mol. Endocrinol., 9:243–54 (1995); GenBank accession number L40372]. Xenopus KSP homologs (Eg5), as well as Drosophila KLP61 F/KRP1 have been reported.

Recently, certain substituted quinazolinones have been described as inhibitors of mitotic kinesins for the treatment of cellular proliferative diseases (WO 01/30768 and WO 01/98278). It is an object of the present invention to provide novel inhibitors of mitotic kinesins such as KSP (particularly human KSP).

SUMMARY OF THE INVENTION

The present invention provides compounds, compositions and methods useful in the inhibition of mitotic kinesins, particularly KSP (more particularly human KSP). The compounds can be used to treat cellular proliferative diseases and include certain pyrrolidin-2-one, piperidin-2-one and tetrahydro-pyrimidin-2-one quinazolinone derivatives.

In one aspect, the invention relates to one or more compounds selected from the group represented by Formula I:

Formula I

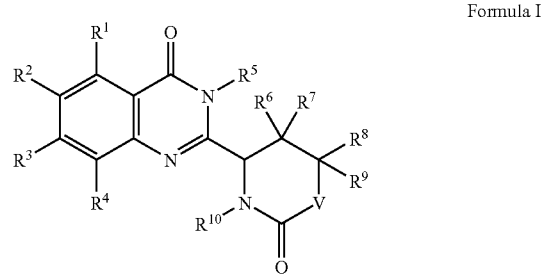

where:
V is chosen from a covalent bond, CR'R" and NR''',
R' and R" being independently chosen from hydrogen, hydroxy, optionally substituted aryl, optionally substituted heteroaryl, optionally substituted amino, optionally substituted alkyl and optionally substituted alkoxy, and
R''' being chosen from hydrogen, optionally substituted alkyl, optionally substituted aryl, optionally substituted aralkyl, optionally substituted heteroaryl, and optionally substituted heteroaralkyl;

$R^1$, $R^2$, $R^3$ and $R^4$ are independently chosen from hydrogen, hydroxy, optionally substituted alkyl, optionally substituted alkoxy, halogen, nitro, optionally substituted amino, alkylsulfonyl, alkylsulfonamido, alkylsulfanyl, alkoxycarbonyl, aminocarbonyl, optionally substituted aryl, optionally substituted heteroaryl, and cyano;

$R^5$ is chosen from hydrogen, optionally substituted alkyl, optionally substituted aryl, optionally substituted aralkyl, optionally substituted heteroaryl, and optionally substituted heteroaralkyl;

$R^6$ to $R^9$ are independently chosen from hydrogen, hydroxy, optionally substituted alkyl, optionally substituted alkoxy, optionally substituted aryl, and optionally substituted alkylamino, provided that neither $R^8$ nor $R^9$ is hydroxy or alkoxy when V is NR'''; and $R^{10}$ is chosen from hydrogen, optionally substituted alkyl, optionally substituted aryl, optionally substituted aralkyl, optionally substituted heteroaryl, and optionally substituted heteroaralkyl;

including single stereoisomers, mixtures of stereoisomers, and pharmaceutically acceptable salts, solvates, and solvates of pharmaceutically acceptable salts thereof. Compounds of Formula I and pharmaceutically acceptable salts and solvates thereof are useful as active agents in the practice of the methods of treatment and in manufacture of compositions including the pharmaceutical formulations of the invention, and may also be useful as intermediates in the synthesis of such active agents.

In another aspect, the invention relates to one or more compounds selected from the group represented by Formula II:

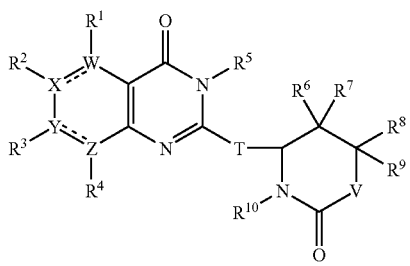

Formula II where:
T is a covalent bond or optionally substituted lower alkylene;
W, X, Y and Z are independently N, C, O, S or absent, provided that:
no more than one of W, X, Y or Z is absent,
no more than two of W, X, Y and Z are —N═, and
W, X, Y or Z can be O or S only when one of W, X, Y or Z is absent; and
$R^1$ to $R^{10}$ and V are as defined with regard to Formula I, provided that $R^1$, $R^2$, $R^3$ or $R^4$ is absent where W, X, Y or Z, respectively, is —N═, O, S or absent;

including single stereoisomers, mixtures of stereoisomers, and pharmaceutically acceptable salts, solvates, and solvates of pharmaceutically acceptable salts thereof. The compounds encompassed by Formula II and pharmaceutically acceptable salts and solvates thereof will be seen to include those of Formula I; they are likewise useful as active agents in the practice of the methods of treatment and in manufacture of compositions including the pharmaceutical formulations of the invention, and may also be useful as intermediates in the synthesis of such active agents.

In one of its particular aspects the present invention pertains to a compound represented by Formula I or II, having a substituent selected from one or more of the following for $R^1$ to $R^4$; $R^5$; $R^6$ to $R^9$; $R^{10}$; T; V; or W, X, Y and Z:

$R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano;

$R^5$ is aralkyl or substituted aralkyl (particularly benzyl or substituted benzyl; most particularly benzyl);

$R^6$ to $R^9$ are hydrogen;

$R^{10}$ is optionally substituted benzyl or optionally substituted phenyl (particularly tolylmethyl);

T is a covalent bond;

V is $CH_2$, N(H) or N(optionally substituted alkyl); and

W, X, Y and Z are —C═.

Other particular aspects of the invention pertain to methods and to pharmaceutical formulations employing such a compound.

In one aspect, the invention relates to methods for treating cellular proliferative diseases, for disorders that can be treated by modulating KSP kinesin activity, and for inhibiting KSP kinesin by the administration of a therapeutically effective amount of a compound of Formula I or II, or a pharmaceutically acceptable salt or solvate of such compounds. Diseases and disorders that respond to therapy with compounds of the invention include cancer, hyperplasia, restenosis, cardiac hypertrophy, immune disorders and inflammation.

In another aspect, the invention relates to a pharmaceutical composition containing a therapeutically effective amount of a compound of Formula I or II or a pharmaceutically acceptable salt or solvate thereof admixed with at least one pharmaceutically acceptable excipient.

Yet another aspect of the invention relates to a kit having a compound, pharmaceutically acceptable salt or solvate of Formula I or II and a package insert or other labeling including directions for treating a cellular proliferative disease by administering an effective amount of the compound, salt or solvate. In one particular such aspect, the compound, pharmaceutically acceptable salt or solvate of Formula I or II is provided as a pharmaceutical composition.

In an additional aspect, the present invention provides methods of screening for compounds that will bind to a KSP kinesin, for example compounds that will displace or compete with the binding of the compounds of the invention. The methods entail combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods entail combining a compound of the invention, a KSP kinesin, and at least one candidate agent and determining the effect of the candidate agent on the KSP kinesin activity.

DETAILED DESCRIPTION OF THE INVENTION

The present invention provides compounds, compositions and methods useful in the inhibition of mitotic kinesins, particularly KSP (more particularly human KSP). The compounds can be used to treat cellular proliferative diseases and include certain pyrrolidin-2-one, piperidin-2-one and tetrahydro-pyrimidin-2-one quinazolinone derivatives. The invention further relates to pharmaceutical formulations comprising compounds of the invention, and methods of treatment employing such compounds or compositions.

Definitions

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| Boc = | t-butyloxy carbonyl |
| Bu = | butyl |
| c- = | cyclo |
| CBZ = | carbobenzoxy = benzyloxycarbonyl |
| DCM = | dichloromethane = methylene chloride = $CH_2Cl_2$ |
| DIEA = | N,N-diisopropylethylamine |
| DMF = | N,N-dimethylformamide |
| DMSO = | dimethyl sulfoxide |
| Et = | ethyl |
| Me = | methyl |
| rt = | room temperature |
| s- = | secondary |
| t- = | tertiary |
| TFA = | trifluoroacetic acid |
| THF = | tetrahydrofuran |

The substituents identified as V, W and Y are intended to have the meanings set forth in the Summary, this Detailed Description and the Claims; they are not intended to designate the atomic elements Vanadium, Tungsten and Yttrium.

The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Alkyl" is intended to include linear, branched, or cyclic aliphatic hydrocarbon structures and combinations thereof, which structures may be saturated or unsaturated (particularly having up to 20 carbon atoms, more particularly up to $C_{13}$.). Lower alkyl refers to alkyl groups of from 1 to 5 (particularly 1 to 4) carbon atoms. Examples of lower alkyl groups include methyl, ethyl, propyl, isopropyl, butyl, s-and t-butyl and the like. Cycloalkyl is a subset of alkyl and includes cyclic aliphatic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene, alkenylene and alkynylene are other subsets of alkyl, referring to the same residues as alkyl, but having two points of attachment. Examples of alkylene include ethylene (—$CH_2CH_2$—), ethenylene (—CH=CH—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers of that residue having the specified number of carbons are meant to be included; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, particularly including from 1 to 8 carbon atoms in a straight, branched or cyclic configuration, or combinations thereof, attached to the parent structure through an oxygen. Examples include methoxy, ethoxy, propoxy, isopropoxy, cyclopropyloxy, cyclohexyloxy and the like. Lower-alkoxy refers to groups containing one to five carbons.

The term "substituted alkoxy" refers to the group —O-(substituted alkyl). One particular substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2–20, particularly about 2–10, and more particularly about 2–5. Another particular substituted alkoxy group is hydroxyalkoxy or —$OCH_2(CH_2)_yOH$, where y is an integer of about 1–10, particularly about 1–4.

"Acyl" refers to groups of from 1 to 8 carbon atoms in a straight, branched or cyclic configuration, or combinations thereof, or to a hydrogen atom attached to the parent structure through a carbonyl functionality. Such groups may be saturated or unsaturated, and aliphatic or aromatic. One or more carbons in the acyl residue may be replaced by nitrogen, oxygen or sulfur as long as the point of attachment to the parent remains at the carbonyl. Examples include formyl, acetyl, benzoyl, propionyl, isobutyryl, t-butoxycarbonyl, benzyloxycarbonyl, aminocarbonyl, and the like. Lower-acyl refers to an acyl group containing one to five carbons. "Substituted acyl" refers to an acyl group where one or more of the hydrogens otherwise attached to a carbon, nitrogen or sulfur atom is substituted, the point of attachment to the parent moiety remaining at the carbonyl.

The term "acyloxy" refers to the group —O-acyl. "Substituted acyloxy" refers to the group —O-substituted acyl.

The term "amidino" refers to the group —C(=NH)—$NH_2$. The term "substituted amidino" refers to the formula —C(=NR)—NRR in which each R is independently selected from the group: hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R is not hydrogen.

The term "amino" refers to the group —$NH_2$. The term "substituted amino" refers to the group —NHR or —NRR where each R is independently selected from the group: optionally substituted acyl, optionally substituted alkyl, optionally substituted alkoxy, optionally substituted amino, optionally substituted aryl, optionally substituted heteroaryl, optionally substituted heterocyclyl, sulfinyl and sulfonyl, e.g., methylamino, dimethylamino, diethylamino, methylsulfonylamino, furanyl-oxy-sulfonamino, guanidino.

"Aryl" and "heteroaryl" mean a 5- or 6-membered aromatic ring or heteroaromatic ring containing 1–4 heteroatoms selected from O, N, or S; a bicyclic 9- or 10-membered aromatic ring system or heteroaromatic ring system containing 1–4 (or more) heteroatoms selected from O, N, or S; or a tricyclic 13- or 14-membered aromatic ring system or heteroaromatic ring system containing 1–4 (or more) heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole; particularly imidazole and imidazoline.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

The term "aryloxy" refers to the group —O-aryl. Similarly, "aralkoxy" and "heteroaralkoxy" refer, respectively, to an aryl or heteroaryl moiety attached to the parent structure via an alkoxy residue.

"Halogen" or "halo" refers to fluorine, chlorine, bromine or iodine (particularly fluorine, chlorine and bromine). Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" or "heterocyclyl" means a cycloalkyl or aryl residue in which one to four of the carbons is replaced by a heteroatom such as oxygen, nitrogen or sulfur (i.e., encompassing heterocycloalkyl and heteroaryl). Examples of heterocyclyl residues that fall within the scope of the invention include imidazolyl, imidazolinyl, pyrrolidinyl, pyrazolyl, pyrrolyl, indolyl, quinolinyl, isoquinolinyl, tetrahydroisoquinolinyl, benzofuranyl, benzodioxanyl, benzodioxolyl (commonly referred to as methylenedioxyphenyl, when occurring as a substituent), tetrazolyl, morpholinyl, thiazolyl, pyridinyl, pyridazinyl, pyrimidinyl, thiophenyl, furanyl, oxazolyl, oxazolinyl, isoxazolyl, dioxanyl, tetrahydrofuranyl and the like. "N-heterocyclyl" refers to a nitrogen-containing heterocycle as a substituent residue. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

The terms "heteroaryloxy" and "heterocyclooxy" refer, respectively to the groups —O-heteroaryl and —O-heterocyclyl.

The term "solvate" refers to a compound (e.g., a compound of Formula I or II or a pharmaceutically acceptable salt thereof) in physical association with one or more molecules of a pharmaceutically acceptable solvent. It will be understood that phrases such as "a compound of Formula I or II or a pharmaceutically acceptable salt or solvate thereof" are intended to encompass the compound of Formula I or II, a pharmaceutically acceptable salt of the compound, a solvate of the compound, and a solvate of a pharmaceutically acceptable salt of the compound.

The term "substituted" as used with regard to alkyl, aryl, aralkyl, heteroaryl and heterocyclyl refers to an alkyl, aryl, aralkyl, heteroaryl or heterocyclyl moiety wherein one or more (up to about 5, particularly up to about 3) hydrogen atoms are replaced by a substituent independently selected from the group: optionally substituted acyl (e.g., aminocarbonyl and alkoxycarbonyl or "esters"), optionally substituted acyloxy (e.g., acid esters, carbamic acid esters, carbonic acid esters, and thiocarbonic acid esters), optionally substituted alkyl (e.g., fluoroalkyl), optionally substituted alkoxy (e.g., methoxy and methoxymethoxy), alkylenedioxy (e.g. methylenedioxy), optionally substituted amino (e.g., alkylamino, dialkylamino, carbonylamino, benzyloxycarbonylamino or "CBZ-amino", and carboxamido), optionally substituted amidino, optionally substituted aryl (e.g., phenyl and 4-methyl-phenyl or "tolyl"), optionally substituted aralkyl (e.g., benzyl), optionally substituted aryloxy (e.g., phenoxy), optionally substituted aralkoxy (e.g., benzyloxy), optionally substituted heteroaryl, optionally substituted heteroaralkyl, optionally substituted heteroaryloxy, optionally substituted heteroaralkoxy, carboxy (—COOH), cyano, halogen, hydroxy, nitro, sulfanyl, sulfinyl, sulfonyl and thio. In the compounds of Formula II where T is substituted alkylene, the term "substituted" also refers to alkylene groups where one or more (up to about 3, particularly 1) carbon atoms are replaced by a heteroatom independently selected from O, N or S, such as —CH$_2$—S—CH$_2$—.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown are designated (+) or (−) depending on the direction (dextro- or levorotatory) which they rotate plane polarized light at the wavelength of the sodium D line. The term "substantially pure" means having at least about 95% chemical purity with no single impurity greater than about 1%. The term "substantially optically pure" or "substantially enantiomerically pure" means having at least about 95% enantiomeric excess. The invention contemplates the use of pure enantiomers and mixtures of enantiomers, including racemic mixtures, although the use of a substantially optically pure enantiomer will generally be most suitable.

"Mitotic spindle formation" refers to the organization of microtubules into bipolar structures by mitotic kinesins. "Mitotic spindle dysfunction" refers to mitotic arrest, monopolar spindle formation or mitotic spindle malformation, in which context "malformation" encompasses the splaying of mitotic spindle poles, or otherwise causing morphological perturbation of the mitotic spindle. The term "inhibit" as used with reference to mitotic spindle formation, means altering mitotic spindle formation, including decreasing spindle formation, and increasing or decreasing spindle pole separation. "Anti-mitotic" means inhibiting or having the potential to inhibit mitosis, for example, as described above.

The term "pharmaceutically acceptable salts" is meant to include both acid and base addition salts. A "pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly suitable are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The term "therapeutically effective amount" or "effective amount" refers to that amount of a compound of Formula I or II that is sufficient to effect treatment, as defined below, when administered to a patient in need of such treatment. The effective amount will vary depending upon the patient and disease condition being treated, the weight and age of the patient, the severity of the disease condition, the particular compound, pharmaceutically acceptable salt or solvate of Formula I or II chosen, the dosing regimen to be followed, timing of administration, the manner of administration and the like, all of which can readily be determined by one of ordinary skill in the art. In a particular aspect of the invention, the effective amount will be an amount sufficient to inhibit KSP kinesin activity in cells involved with the disease being treated.

The term "treatment" or "treating" means any treatment of a disease in a patient, including:
a) preventing the disease, that is, causing the clinical symptoms of the disease not to develop;
b) inhibiting the disease, that is, slowing or arresting the development of clinical symptoms; and/or
c) relieving the disease, that is, causing the regression of clinical symptoms.

A "patient" for the purposes of the present invention includes humans and other animals, particularly mammals, and other organisms. Thus the methods are applicable to both human therapy and veterinary applications. In a particular embodiment the patient is a mammal, most particularly the patient is human.

Compounds of the Present Invention

The present invention provides certain quinazolinone derivatives. The compounds are inhibitors of one or more mitotic kinesins. The present invention capitalizes on the finding that perturbation of mitotic kinesin function causes malformation or dysfunction of mitotic spindles, frequently resulting in cell cycle arrest and cell death.

Accordingly, the present invention relates to one or more compounds selected from the group represented by Formula I:

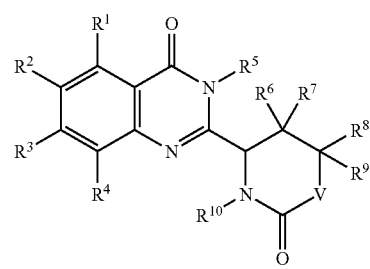

Formula I where:
V is chosen from a covalent bond, CR'R" and NR'",
R' and R" being independently chosen from hydrogen, hydroxy, amino, optionally substituted aryl, optionally substituted alkylamino, optionally substituted alkyl and optionally substituted alkoxy, and
R'" being chosen from hydrogen, optionally substituted alkyl, optionally substituted aryl, optionally substituted aralkyl, optionally substituted heteroaryl, and optionally substituted heteroaralkyl;
$R^1$, $R^2$, $R^3$ and $R^4$ are independently chosen from hydrogen, hydroxy, optionally substituted alkyl, optionally substituted alkoxy, halogen and cyano;
$R^5$ is chosen from hydrogen, optionally substituted alkyl, optionally substituted aryl, optionally substituted aralkyl, optionally substituted heteroaryl, and optionally substituted heteroaralkyl;
$R^6$ to $R^9$ are independently chosen from hydrogen, hydroxy, optionally substituted alkyl, optionally substituted alkoxy, optionally substituted aryl, and optionally substituted alkylamino, provided that neither $R^8$ nor $R^9$ is hydroxy or alkoxy when V is NR'"; and
$R^{10}$ is chosen from hydrogen, optionally substituted alkyl, optionally substituted aryl, optionally substituted aralkyl, optionally substituted heteroaryl, and optionally substituted heteroaralkyl, and the pharmaceutically acceptable salts and solvates thereof.

In another aspect, the invention relates to one or more compounds selected from the group represented by Formula II:

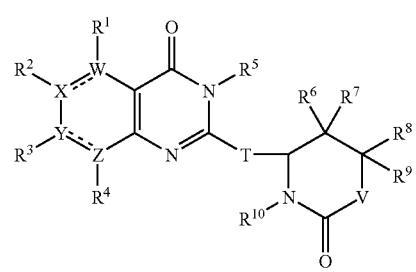

Formula II where:
  $R^1$ to $R^{10}$ and V are as defined with regard to Formula I;
  T is a covalent bond or optionally substituted lower alkylene;
  W, X, Y and Z are independently N, C, O, S or absent, provided that:
    no more than one of W, X, Y or Z is absent,
    no more than two of W, X, Y and Z are —N═, and
    W, X, Y or Z can be O or S only when one of W, X, Y or Z is absent; and
  $R^1$ to $R^{10}$ and V are as defined with regard to Formula I, provided that $R^1$, $R^2$, $R^3$ or $R^4$ is absent where W, X, Y or Z, respectively, is —N═, O, S or is absent, including single stereoisomers, mixtures of stereoisomers, and the pharmaceutically acceptable salts, solvates, and solvates of pharmaceutically acceptable salts thereof. The compounds encompassed by Formula II will be seen to include those of Formula I; they are likewise useful as active agents in the practice of the methods of treatment and in manufacture of compositions including the pharmaceutical formulations of the invention, and may also be useful as intermediates in the synthesis of such active agents. For the sake of simplicity in the following description and claims, substituents T, W, X, Y and Z will not be discussed in connection with certain compounds falling within the scope of Formula I.

Many of the compounds described herein contain one or more asymmetric centers and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that such compounds include both E and Z geometric isomers. All tautomeric forms are also intended to be included. The present invention is meant to include all such possible isomers, including racemic mixtures, intermediate mixtures, optically pure forms, substantially optically pure forms, enantiomerically pure forms, and substantially enantiomerically pure forms.

Nomenclature

The compounds of Formula I and II can be named and numbered (e.g., using AutoNom version 2.1 in ISIS-DRAW or ChemDraw) as described below.

For example, the compound of Formula IA:

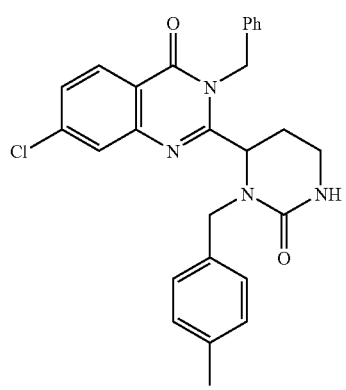

Formula IA i.e., the compound according to Formula I where $R^1$, $R^2$ and $R^4$ are H; $R^3$ is chloro; $R^5$ is benzyl; $R^6$ to $R^9$ are H; $R^{10}$ is 4-methyl-benzyl; and V is NH, can be named 3-benzyl-7-chloro-2-[3-(4-methyl-benzyl)-2-oxo-hexahydro-pyrimidin-4-yl]-3H-quinazolin-4-one.

The compound of Formula IB:

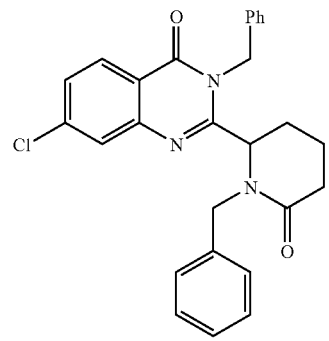

Formula IB i.e., the compound according to Formula I where $R^1$, $R^2$ and $R^4$ are H; $R^3$ is chloro; $R^5$ is benzyl; $R^6$ to $R^9$ are H; $R^{10}$ is benzyl; and V is $CH_2$, can be named 3-benzyl-2-(1-benzyl-6-oxo-piperidin-2-yl)-7-chloro-3H-quinazolin-4-one.

The compound of Formula IIA:

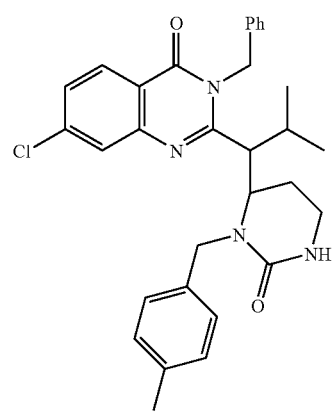

Formula IIA i.e., the compound according to Formula II where $R^1$, $R^2$ and $R^4$ are H; $R^3$ is chloro; $R^5$ is benzyl; $R^6$ to $R^9$ are H; $R^{10}$ is 4-methyl-benzyl; T is isopropyl-methylene; V is NH; and W, X, Y and Z are —C═, can be named 3-benzyl-7-chloro-2-{2-methyl-1-[3-(4-methyl-benzyl)-2-oxo-hexadydro-pyrimidin-4-yl]-propyl}-3H-quinazolin-4-one.

The compound of Formula IIB:

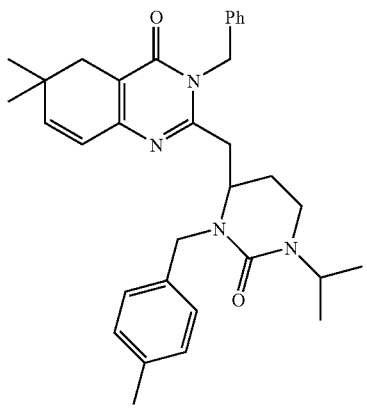

Formula IIB i.e., the compound according to Formula II where $R^1$, $R^3$ and $R^4$ are H; $R^2$ is di-methyl; $R^5$ is benzyl; $R^6$ to $R^9$ are H; $R^{10}$ is 4-methyl-benzyl; T is methylene; V is NR''' where R''' is isopropyl; and W is $CH_2$, X is C, and Y and Z are —C=, can be named 3-benzyl-2-[1-isopropyl-3-(4-methyl-benzyl)-2-oxo-hexahydro-pyrimidin-4-ylmethyl]-6,6-dimethyl-5,6-dihydro-3H-quinazolin-4-one.

The compound of Formula IIC:

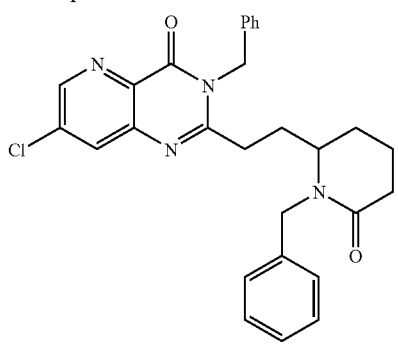

Formula IIC i.e., the compound according to Formula II where $R^1$, $R^2$ and $R^4$ are H; $R^3$ is chloro; $R^5$ is benzyl; $R^6$ to $R^9$ are H; $R^{10}$ is 4-methyl-benzyl; T is ethylene; V is $CH_2$; W is —N=, and X, Y and Z are —C=, can be named 3-benzyl-2-[2-(1-benzyl-6-oxo-piperidin-2-yl)-ethyl]-7-chloro-3H-pyrido[3,2-d]pyrimidin-4-one.

The compound of Formula IID:

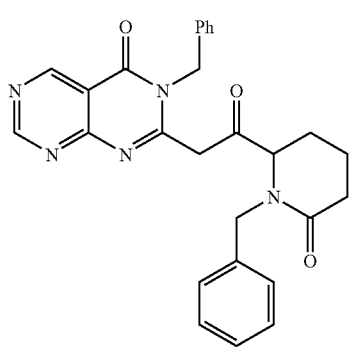

Formula IID i.e., the compound according to Formula II where $R^1$ and $R^3$ are H; $R^2$ and $R^4$ are absent; $R^5$ is benzyl; $R^6$ to $R^9$ are H; $R^{10}$ is benzyl; T is oxo-ethylene; V is NH; and W and Y are —C=; and X and Z are —N=, can be named 3-benzyl-2-[2-(1-benzyl-6-oxo-piperidin-2-yl)-2-oxo-ethyl]-3H-pyrimidino[4,5-d]pyrimidin-4-one.

The compound of Formula IIE:

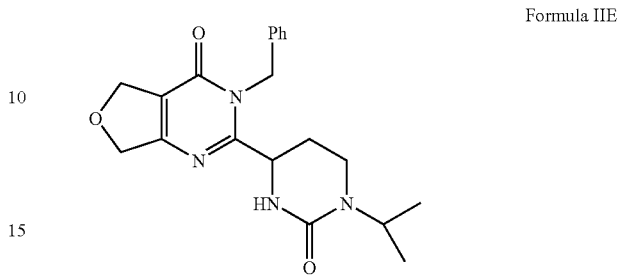

Formula IIE i.e., the compound according to Formula II where $R^1$ and $R^3$ are H; $R^2$ and $R^4$ are absent; $R^5$ is benzyl; $R^6$ to $R^{10}$ are H; T is a covalent bond; V is NR''' where R''' is isopropyl; and W and Y are C; X is O, and Z is absent, can be named 3-benzyl-2-(1-isopropyl-2-oxo-hexahydro-pyrimidin-4-yl)-5,7-dihydro-3H-furo[3,4-d]pyrimidin-4-one.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)- and (S)-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I or II can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Synthesis of the Compounds of Formula I and II

Syntheses of the compounds of Formula I and II are described below with reference to Reaction Schemes 1 to 4.

Brief Description Of Reaction Schemes

Reaction Scheme 1 illustrates a synthesis of the N,N-optionally mono- or di-substituted pyrimidin-2-one compounds of Formula I or II.

Reaction Scheme 2 illustrates a synthesis of intermediates in preparation of the N-optionally substituted piperidin-2-one compounds of Formula I or II.

Reaction Scheme 3 illustrates a synthesis of intermediates in preparation of the N-optionally mono-substituted pyrimidin-2-one compounds of Formula I or II (i.e., where the optional substituent is at $R^{10}$ and V is NH).

Reaction Scheme 4 illustrates a synthesis of the compounds of Formula I or II from the intermediates prepared according to Reaction Schemes 2 and 3.

It will be appreciated by those skilled in the art that one or more of the reaction steps and/or conditions described with reference to Reaction Schemes 1 to 4 may require adjustment to accommodate non-hydrogen substituents at R', R'' and $R^1$ to $R^9$.

Starting Materials

The N-protected 2,4-di-amino butyric acids of Formula 101 (e.g., 4-tert-butoxycarbonylamino-2-(9H-fluoren-9-yl-methoxycarbonylamino)-butyric acid), the anthranilic acids of Formula 102 (e.g., 4-chloro-anthranilic acid), aminoadipic acid hydrate, di-aminobutyric acid and the like are commercially available, e.g., from Aldrich Chemical Company, Milwaukee, Wis. Other reactants are likewise commercially available or may be readily prepared by those skilled in the art using commonly employed synthetic methodology.

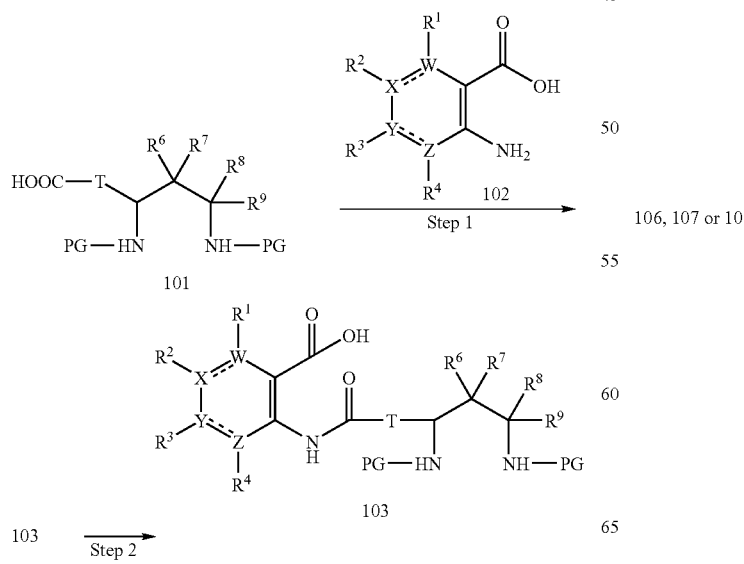

Reaction Scheme 1

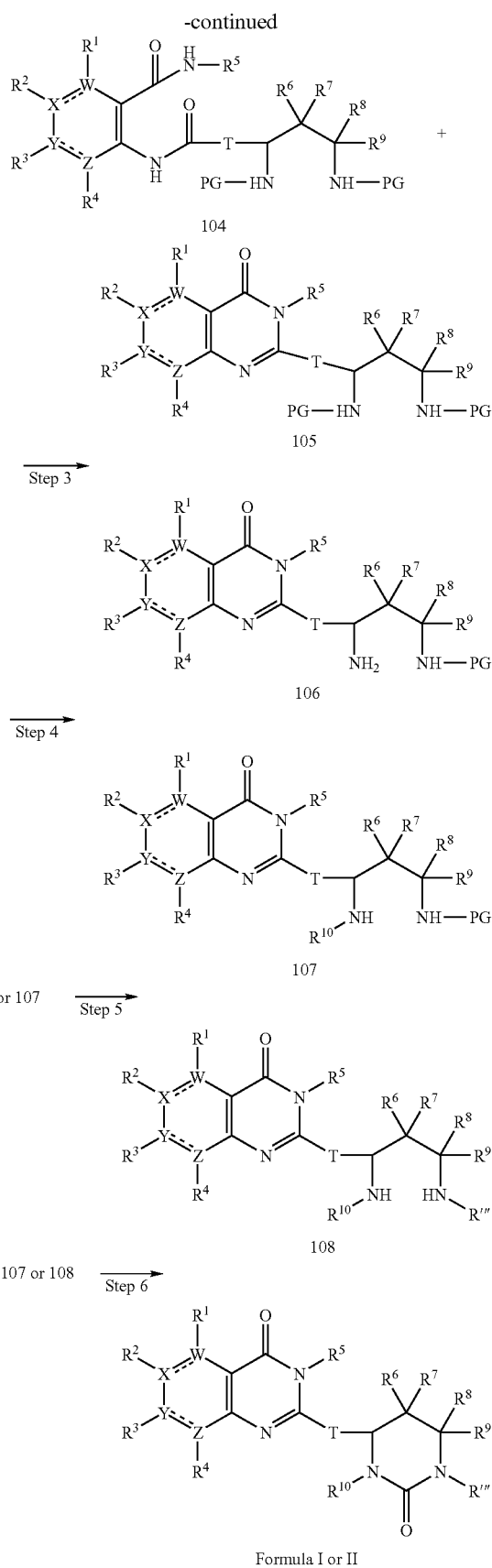

Preparation of Formula 103 Referring to Reaction Scheme 1, Step 1, to an N-protected di-amino lower alkyl acid of Formula 101 (e.g., a protected 2,4-di-amino butyric acid, particularly employing orthogonal amino-protecting groups "PG," such as Fmoc and Boc, to facilitate selective de-protection) in solution with an organic solvent (such as anhydrous THF) is added a slight molar excess of N-methylmorpholine, at reduced temperature (e.g., in an ice bath), followed by the addition of a slight molar excess of isobutyl chloroformate, dropwise over 15 minutes. The mixture is stirred at reduced temperature (e.g., 0° C.) for an hour, followed by the addition of a molar equivalent of an optionally substituted o-amino allocyclic, heterocyclic or (hetero) aryl acid of Formula 102 (such as anthranilic acid) with continued stirring for another 2 hours at reduced temperature. The resulting protected alkylamino-optionally substituted cyclic acid of Formula 103 can be carried forward without isolation or purification.

Preparation of Formula 106 Referring to Reaction Scheme 1, Step 2, to the intermediate of Formula 103 is added a slight molar excess of N-methylmorpholine, and the mixture is allowed to warm to room temperature with continued stirring over 16 hours. The mixture is then cooled to 0° C. and treated with a slight molar excess of both N-methylmorpholine and isobutyl chloroformate, followed by the room temperature addition of about 1.5 molar equivalents of a primary amine of formula $R^5NH_2$ (such as benzylamine) in several equal portions. Removal of the solvents, partitioning between DCM and saturated sodium bicarbonate and drying of the organic layer affords a mixture of Formula 104 and Formula 105, which (in Step 3) is subsequently dried and treated with a molar equivalent of lithium hydroxide monohydrate in a solvent (e.g., 2/1 1,4-dioxane/ethylene glycol) at reflux for 5 hours. The reaction is quenched with water and the desired substituted bi-cyclic product of Formula 106 (e.g., a quinazolinone) is extracted with dichloromethane, dried, and purified (e.g., by flash silica gel chromatography).

Preparation of Formula 107 Referring to Reaction Scheme 1, Step 4, to a solution of a compound of Formula 106 (e.g., in dichloromethane) is added a molar equivalent of a substituted aldehyde (e.g., p-tolualdehyde or benzaldehyde). The mixture is stirred for 1 hour after which a molar excess of sodium triacetoxyborohydride is added with continued stirring for an additional 3 hours. The corresponding 3-substituted amino compound of Formula 107 is conventionally isolated and purified.

Preparation of Formula 108 Referring to Reaction Scheme 1, Step 5, a compound of Formula 107 is deprotected (e.g., in the case where the protecting group PG is t-BOC, by dissolution in aqueous TFA) and stirred for 30 minutes, followed by evaporation of the solvents, partitioning of the residue and drying of the organic layer. The dried residue, and molar excesses of DIEA, sodium triacetoxyborohydride and an R'''-acyl compound (e.g., t-butyl N-(2-oxoethyl) carbamate) are mixed in a solvent (e.g., DCM) and stirred for 1 hour. The solution is washed, dried and evaporated to give the corresponding N—$R^{10}$,N—R'-disubstituted compound of Formula 108. As will be appreciated by those skilled in the art, this step can be omitted in the synthesis of compounds of Formula I or II where R''' is hydrogen, proceeding directly to either of Step 6 with the compound of Formula 106 or 107.

Preparation of Formula I or II Referring to Reaction Scheme 1, Step 6, to a solution of Formula 106, 107 or 108 (e.g., in dichloromethane) is added a molar excess of carbonyldiimidazole, and the reaction is stirred for 1 hour. Evaporation of the solvent and purification (e.g., by silica gel chromatography) gives the corresponding compound of Formula I or II. Where the starting material of Formula 108 is protected (e.g., where R' is NHBoc-ethylene) the protecting group is removed (e.g., dissolving the crude compound of Formula 1 in 95/5 TFA/$H_2O$ with stirring for 1 hour) and the corresponding compound of Formula I or II is conventionally isolated and purified.

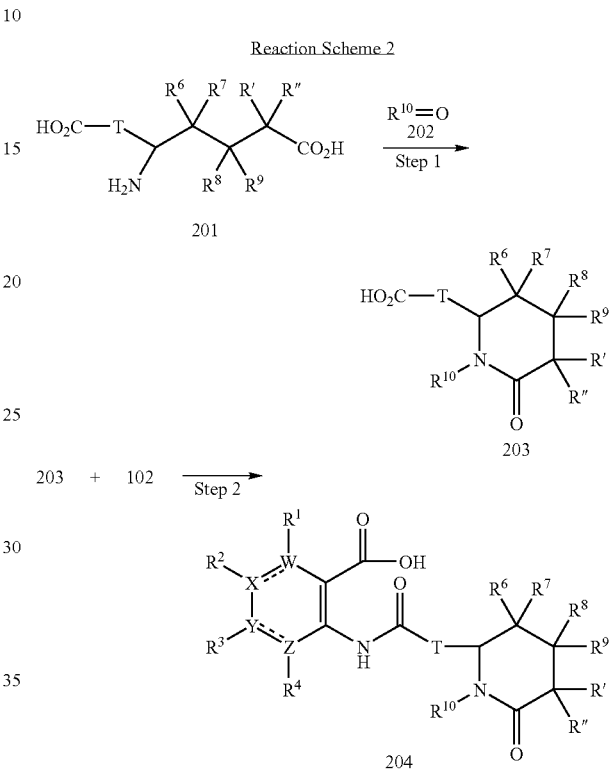

Preparation of Formula 203 In Reaction Scheme 2, Step 1, to a solution of an optionally substituted amino-dicarboxylic acid of Formula 201 (e.g., aminoadipic acid hydrate dissolved in 2 molar equivalents of 2 M NaOH) is added a molar equivalent of a solution of an aldehyde of Formula 202 (e.g., dissolved in ethanol). After 10 minutes the mixture is cooled (e.g., to 0° C.) and sodium borohydride (0.3 molar equivalents) is added. Completion of the reaction is monitored, e.g., by LCMS, followed by extraction and isolation of a crude precipitate product, which is dissolved in ethanol and boiled for 16 hours to afford the corresponding lactam intermediate of Formula 203, which can be carried forward without further purification. By substituting the compound of Formula 201 with an optionally substituted 2-aminopentanedioic acid, the corresponding intermediates of Formula 203 are obtained for the synthesis of Formula I or II where V is a covalent bond.

Preparation of Formula 204 In Reaction Scheme 2, Step 2, the lactam of Formula 203 and a molar equivalent of DIEA are dissolved (e.g., in dichloromethane) and cooled (e.g., to 0° C.). One molar equivalent of isobutyl chloroformate is added and the mixture stirred (e.g., for 20 minutes) followed by addition of 2 additional molar equivalents of DIEA followed by a slight molar excess of an optionally substituted o-amino-acid of Formula 102. The reaction takes place, warming to room temperature, over 16 hours, to afford the corresponding acid of Formula 204 (also a compound of Formula 401), which is washed, dried, evaporated, re-washed, cooled (e.g., to 0° C.), acidified and then isolated for subsequent use without further purification.

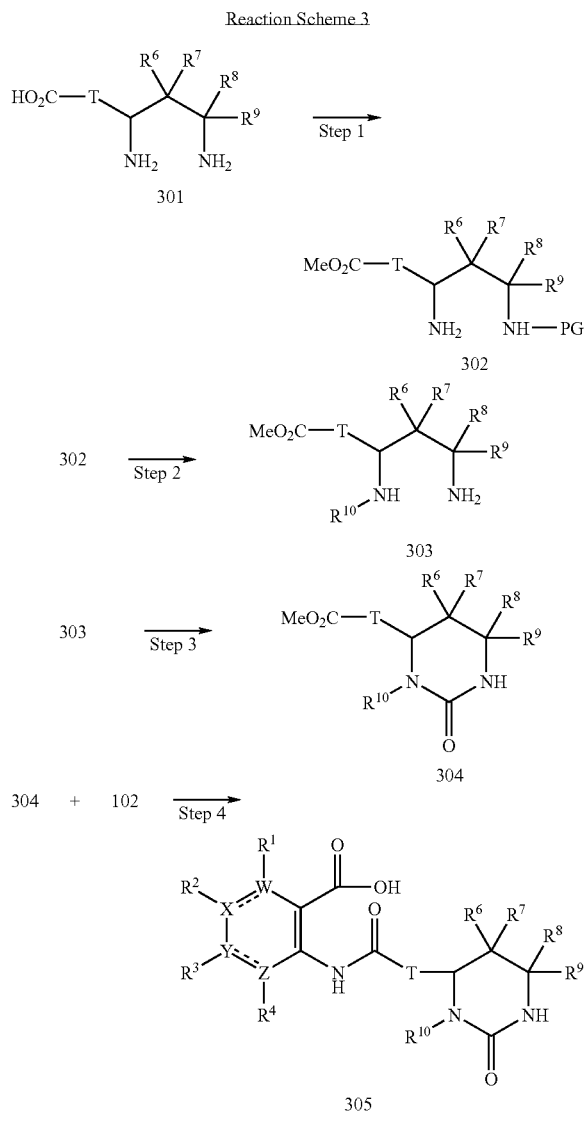

Preparation of Formula 302 In Reaction Scheme 3, Step 1, an optionally substituted diamino lower alkyl acid of Formula 301 and 3 molar equivalents of sodium bicarbonate are dissolved in water, to which one-half molar equivalent of copper sulfate dissolved in water is added. A molar excess of di-(tert-butyl) pyrocarbonate (dissolved, e.g., in acetone) is added followed by stirring for 24 hours, the addition of methanol and continued stirring for another 18 hours. The resulting intermediate mono-Boc-protected copper complex is filtered, washed and dried, then suspended in water. Two molar equivalents of quinolol are added to the suspension. After 5 hours, the suspension is filtered off and the liquid is evaporated. The solid thus-obtained is dissolved (e.g., in 200 mL of 30% methanol in benzene), and (trimethylsilyl) diazomethane is added, dropwise to completion (indicated by color change and cessation of bubbling), followed by stirring for 1 hour and the dropwise addition of acetic acid to completion (indicated, e.g., by color change and cessation of bubbling). The resulting material is purified conventionally to provide the corresponding methyl ester of Formula 302.

Preparation of Formula 303 In Reaction Scheme 3, Step 2, to a solution of Formula 302 (e.g., in DCM) is added almost one molar equivalent of an $R^{10}$-aldehyde (e.g., p-tolualdehyde or benzaldehyde) and the mixture stirred at room temperature for 1 hour. A slight molar excess of sodium triacetoxyborohydride is added and the mixture is stirred for 16 hours. The protecting group is removed (e.g., dissolving the $R^{10}$-substituted amine in 2M HCl in dioxane solution followed by stirring for 2 hours). The solution is then washed, dried, isolated and purified conventionally to give the corresponding optionally substituted-aminomethyl ester compound of Formula 303.

Preparation of Formula 304 In Reaction Scheme 3, Step 3, to a solution of Formula 303 and 2 molar equivalents of DIEA (e.g., in DCM) is added a molar excess of carbonyldiimidazole. The reaction mixture is stirred for 1 hour, after which the solvents are evaporated. The residue is dissolved (e.g., in MeOH:$H_2O$ (2:1) solution) to which solution is was added 2 molar equivalents of LiOH. The reaction takes place with stirring over 3 hours after which pH is adjusted to ~7 (e.g., by adding Dowex-H+ resin). Conventional isolation and purification gives the corresponding pyrimidine of Formula 304.

Preparation of Formula 305 In Reaction Scheme 3, Step 4, to a solution of Formula 304 (e.g., in DMF) is added a slight molar excess of anhydrous N-methylmorpholine. After cooling in an ice-bath for 10 minutes, a slight molar excess of isobutyl chloroformate is added dropwise while maintaining the temperature below 5° C. with stirring for 1 hour. A slight molar excess of an optionally substituted o-amino allocyclic, heterocyclic or (hetero)aryl acid of Formula 102 (such as anthranilic acid) of Formula 102 (dissolved, e.g., in DMF) is added and the mixture stirred for an additional 5 hours during which the temperature is allowed to warm to room temperature to afford the corresponding intermediate product of Formula 305 (also a compound of Formula 401), which can be carried on without isolation or purification.

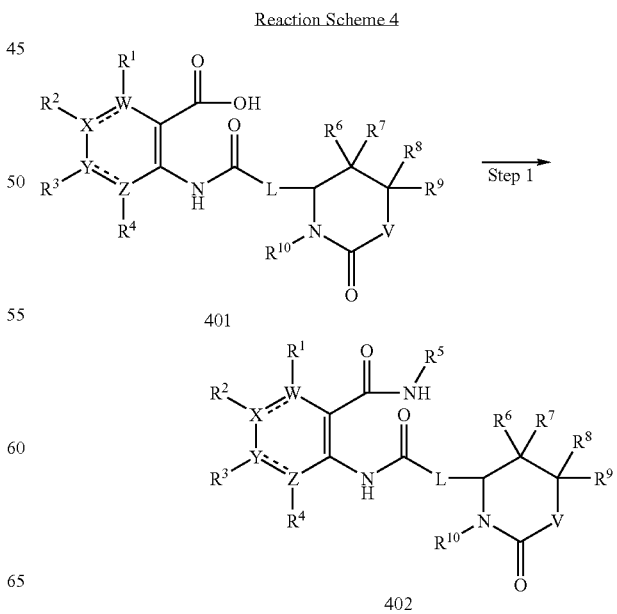

-continued

402 $\xrightarrow{\text{Step 2}}$

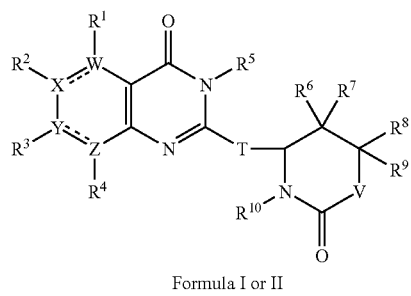

Formula I or II

Preparation of Formula 402 and Formula I or II In Reaction Scheme 4, Step 1, to a solution of a piperidine compound of Formula 401 (e.g., in DMF) is added 3 molar equivalents of EDC followed by stirring at room temperature for 1 hour. Three molar equivalents of an $R^5$-amine (e.g., benzylamine) are added followed by stirring for an additional 3 hours. Conventional isolation and purification provides the corresponding crude intermediate of Formula 402. In Reaction Scheme 4, Step 2, the compound of Formula 402 is added to a mixture of ethylene glycol with 1 molar equivalent of sodium hydroxide, followed by stirring at 130° C. for two days. The mixture is then poured into water, extracted and purified to give the corresponding pure product of Formula I or II.

Alternative Preparation of Formula 402 and Formula I or II Alternatively, in Reaction Scheme 4, Step 1, two molar equivalents of EDC are added to a solution of a pyrimidine compound of Formula 401 (e.g., in DMF) followed by stirring for 1 hour and then by the addition of an $R^5$-amine (e.g., benzylamine). The resulting solution is stirred for 16 hours and the corresponding compound of Formula 402 is isolated and purified conventionally. In Reaction Scheme 4, Step 2, the compound of Formula 402 is dissolved (e.g., in ethylene glycol to which was added 2 molar equivalents of sodium hydroxide). The mixture is stirred at 140° C. for 20 hours. Following consumption of starting material, the reaction mixture is poured into 100 mL of water. After extraction with DCM, the crude product is isolated and purified conventionally to give the corresponding pure product of Formula I or II.

Compounds prepared by the above-described process of the invention may be identified by the presence of a detectable amount of Formula 402. While it is well known that pharmaceuticals must meet pharmacopoeia standards before approval and/or marketing, and that synthetic reagents (such as benzylamine, ethylene glycol or NaOH) and precursors (such as Formula 402) should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

Particular Optional Processes and Last Steps

A compound of Formula 402 is dissolved in an organic solvent (e.g., ethylene glycol) to which was added about 2 molar equivalents of sodium hydroxide.

A protected amino-substituted precursor to Formula I or II (e.g.,. where R''' or $R^{10}$ is NHBoc-protected amino ethyl) is dissolved in TFA/$H_2O$ and stirred to afford the corresponding de-protected compound of Formula I or II.

A racemic mixture of isomers of a compound of Formula I or II is placed on a chromatography column and separated into (R)— and (S)— enantiomers.

A compound of Formula I or II is contacted with a pharmaceutically acceptable acid to form the corresponding acid addition salt.

A pharmaceutically acceptable acid addition salt of Formula I or II is contacted with a base to form the corresponding free base of Formula I or II.

Particular Compounds

Particular embodiments of the invention include or employ the compounds of Formula I and II having the following combinations and permutations of substituent groups (indented/sub-grouped, respectively, in increasing order of particularity). These are presented in support of the appended claims as well as combinations and permutations of substituent groups that may, for the sake of brevity, not be specifically claimed but should be appreciated as encompassed by the teachings of the present disclosure. In that regard, the described subsets for each substituent are intended to apply to that substituent alone or in combination with one, several, or all of the described subsets for the other substituents, for example, as illustrated with regard to the compounds where V is CR'R'' or NR'''.

W, X, Y and Z are independently chosen from —C═and —N═;
  W, X, Y and Z are —C═.
$R^1$, $R^2$, $R^3$ and $R^4$ are independently chosen from hydrogen, halo (especially chloro and fluoro), lower alkyl (especially methyl), substituted lower alkyl, lower alkoxy (especially methoxy), and cyano.
  $R^1$, $R^2$, $R^3$ and $R^4$ are independently hydrogen, chloro, fluoro, methyl, methoxy or cyano.
    Where three or four of $R^1$, $R^2$, $R^3$ and $R^4$ are hydrogen.
      Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
        Where halo is chloro.
          Where $R^3$ is hydrogen or chloro.
            Where $R^3$ is chloro.
$R^5$ is optionally substituted aralkyl.
  $R^5$ is benzyl or substituted benzyl.
    $R^5$ is benzyl.
$R^6$ is hydrogen or optionally substituted lower alkyl.
  $R^6$ is hydrogen.
$R^7$ is hydrogen or optionally substituted lower alkyl.
  $R^7$ is hydrogen.
$R^8$ is hydrogen or optionally substituted lower alkyl.
  $R^8$ is hydrogen.
$R^9$ is hydrogen or optionally substituted lower alkyl.
  $R^9$ is hydrogen.
$R^{10}$ is optionally substituted aryl or optionally substituted aralkyl.
  $R^{10}$ is optionally substituted phenyl or optionally substituted benzyl.

$R^{10}$ is benzyl or methyl-benzyl.
T is optionally substituted $C_1$ to $C_4$ alkylene or is absent.
  T is absent.
  Where T is alkylene having a carbon substituted by a heteroatom, the heteroatom is not bound directly to the bicyclic structure.
    T is aminoalkylene or amidoalkylene.
  T is alkylene or alkylene substituted with halo or oxo.
V is CR'R" or NR'".
  V is CR'R" (particularly where R' and/or R" are hydrogen).
    Where R' and R" are hydrogen.
    Where W, X, Y and Z are independently chosen from —C= and —N=.
      W, X, Y and Z are —C=.
      Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
        $R^1$, $R^2$, $R^3$ and $R^4$ are independently hydrogen, chloro, fluoro, methyl, methoxy or cyano.
        Where three or four of $R^1$, $R^2$, $R^3$ and $R^4$ are hydrogen.
          Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
          Where halo is chloro.
          Where $R^3$ is chloro.
          Where R' and R" are hydrogen.
    Where $R^5$ is optionally substituted aralkyl.
      Where $R^5$ benzyl or substituted benzyl.
        Where $R^5$ is benzyl.
        Where R' and R" are hydrogen.
    Where $R^6$, $R^7$, $R^8$ and $R^9$ are independently chosen from hydrogen or optionally substituted lower alkyl.
      Where at least three of $R^6$, $R^7$, $R^8$ and $R^9$ are hydrogen.
        Where $R^6$, $R^7$, $R^8$ and $R^9$ are hydrogen.
        Where R' and R" are hydrogen.
    Where $R^{10}$ is optionally substituted aryl or optionally substituted aralkyl.
      $R^{10}$ is optionally substituted phenyl or optionally substituted benzyl.
        $R^{10}$ is benzyl or methyl-benzyl.
        Where R' and R" are hydrogen.
  Where W, X, Y and Z are chosen from —C= and —N=.
    W, X, Y and Z are —C=.
      Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
        $R^1$, $R^2$, $R^3$ and $R^4$ are independently hydrogen, chloro, fluoro, methyl, methoxy or cyano.
        Where three or four of $R^1$, $R^2$, $R^3$ and $R^4$ are hydrogen.
          Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
          Where halo is chloro.
          Where $R^3$ is chloro.
  Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
    $R^1$, $R^2$, $R^3$ and $R^4$ are independently hydrogen, chloro, fluoro, methyl, methoxy or cyano.
    Where three or four of $R^1$, $R^2$, $R^3$ and $R^4$ are hydrogen.
      Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where halo is chloro.
      Where $R^3$ is chloro.
  Where $R^5$ is optionally substituted aralkyl.
    Where $R^5$ is benzyl or substituted benzyl.
      Where $R^5$ is benzyl.
  Where $R^6$, $R^7$, $R^8$ and $R^9$ are independently chosen from hydrogen or optionally substituted lower alkyl.
    Where at least three of $R^6$, $R^7$, $R^8$ and $R^9$ are hydrogen.
      Where $R^6$, $R^7$, $R^8$ and $R^9$ are hydrogen.
  Where $R^{10}$ is optionally substituted aryl or optionally substituted aralkyl.
    $R^{10}$ is optionally substituted phenyl or optionally substituted benzyl.
      $R^{10}$ is benzyl or methyl-benzyl.
  Where T is optionally substituted $C_1$ to $C_4$ alkylene or is absent.
    T is absent.
    Where T is alkylene having a carbon substituted by a heteroatom, the heteroatom is not bound directly to the bicyclic structure.
      T is aminoalkylene or amidoalkylene.
    T is alkylene or alkylene substituted with halo or oxo.
V is NR'" (particularly where R'" is hydrogen or optionally substituted alkyl).
  Where R'" is hydrogen or optionally substituted amino-lower alkyl.
  Where W, X, Y and Z are chosen from —C= and —N=.
    W, X, Y and Z are —C=.
    Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
      $R^1$, $R^2$, $R^3$ and $R^4$ are independently hydrogen, chloro, fluoro, methyl, methoxy or cyano.
      Where three or four of $R^1$, $R^2$, $R^3$ and $R^4$ are hydrogen.
        Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
        Where halo is chloro.
        Where $R^3$ is chloro.
        Where R'" is hydrogen or amino-lower alkyl.
  Where $R^5$ is optionally substituted aralkyl.
    Where $R^5$ is benzyl or substituted benzyl.
      Where $R^5$ is benzyl.
    Where R'" is hydrogen or optionally substituted amino-lower alkyl.
  Where $R^6$, $R^7$, $R^8$ and $R^9$ are independently chosen from hydrogen or optionally substituted lower alkyl.
    Where at least three of $R^6$, $R^7$, $R^8$ and $R^9$ are hydrogen.
      Where $R^6$, $R^7$, $R^8$ and $R^9$ are hydrogen.
        Where R'" is hydrogen or amino-lower alkyl.

Where $R^{10}$ is optionally substituted aryl or optionally substituted aralkyl.
$R^{10}$ is optionally substituted phenyl or optionally substituted benzyl.
$R^{10}$ is benzyl or methyl-benzyl.
Where R''' is hydrogen or amino-lower alkyl.
Where W, X, Y and Z are chosen from —C= and —N=.
W, X, Y and Z are —C=.
Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
$R^1$, $R^2$, $R^3$ and $R^4$ are independently hydrogen, chloro, fluoro, methyl, methoxy or cyano.
Where three or four of $R^1$, $R^2$, $R^3$ and $R^4$ are hydrogen.
Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
Where halo is chloro.
Where $R^3$ is chloro.
Where $R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano.
$R^1$, $R^2$, $R^3$ and $R^4$ are independently hydrogen, chloro, fluoro, methyl, methoxy or cyano.
Where three or four of $R^1$, $R^2$, $R^3$ and $R^4$ are hydrogen.
Where four of $R^1$, $R^2$, $R^3$ and $R^4$ are hydrogen or three of $R^1$, $R^2$, $R^3$ and $R^4$ are hydrogen and the fourth is halo, methoxy, methyl, or cyano.
Where halo is chloro.
Where $R^3$ is chloro.
Where $R^5$ is optionally substituted aralkyl.
Where $R^5$ is benzyl or substituted benzyl.
Where $R^5$ is benzyl.
Where $R^6$, $R^7$, $R^8$ and $R^9$ are independently chosen from hydrogen or optionally substituted lower alkyl.
Where at least three of $R^6$, $R^7$, $R^8$ and $R^9$ are hydrogen.
Where $R^6$, $R^7$, $R^8$ and $R^9$ are hydrogen.
Where $R^{10}$ is optionally substituted aryl or optionally substituted aralkyl.
$R^{10}$ is optionally substituted phenyl or optionally substituted benzyl.
$R^{10}$ is benzyl or methyl-benzyl.
Where T is optionally substituted $C_1$ to $C_4$ alkylene or is absent.
T is absent.
Where T is alkylene having a carbon substituted by a heteroatom, the heteroatom is not bound directly to the bicyclic structure.
T is aminoalkylene or amidoalkylene.
T is alkylene or alkylene substituted with halo or oxo.

Compounds where V is CR'R'' or NR''', including those illustrated by the above-described groupings and sub-groups of substituents, individually and/or combined together, are particularly suitable for practice of the present invention.

One group of compounds, pharmaceutically acceptable salts and solvates thereof, compositions including pharmaceutical formulations, and methods of manufacture and use of the present invention are those wherein the compound of Formula I or II is selected from:
3-benzyl-7-chloro-2-[3-benzyl-2-oxo-hexahydro-pyrimidin-4-yl]-3H-quinazolin-4-one;
3-benzyl-7-chloro-2-[3-(4-methyl-benzyl)-2-oxo-hexahydro-pyrimidin-4-yl]-3H-quinazolin-4-one;
3-benzyl-2-(1-benzyl-6-oxo-piperidin-2-yl)-7-chloro-3H-quinazolin-4-one;
3-benzyl-2-(1-(4-methyl-benzyl)-6-oxo-piperidin-2-yl)-7-chloro-3H-quinazolin-4-one; and
2-[-1-(2-amino-ethyl)-3-(4-methyl-benzyl)-2-oxo-hexahydro-pyrimidin-4-yl]-3-benzyl-7-chloro-3H-quinazolin-4-one.

A particular group of compounds, pharmaceutically acceptable salts and solvates thereof, compositions including pharmaceutical formulations, and methods of manufacture and use of the present invention are those wherein the compound of Formula I or II is selected from:
3-benzyl-7-chloro-2-[3-(4-methyl-benzyl)-2-oxo-hexahydro-pyrimidin-4-yl]-3H-quinazolin-4-one;
3-benzyl-2-(1-benzyl-6-oxo-piperidin-2-yl)-7-chloro-3H-quinazolin-4-one; and
3-benzyl-2-(1-(4-methyl-benzyl)-6-oxo-piperidin-2-yl)-7-chloro-3H-quinazolin-4-one.

Another particular group of compounds, pharmaceutically acceptable salts and solvates thereof, compositions including pharmaceutical formulations, and methods of manufacture and use of the present invention are those wherein the compound of Formula I or II is selected from:
3-benzyl-2-(1-benzyl-6-oxo-piperidin-2-yl)-7-chloro-3H-quinazolin-4-one; and
3-benzyl-2-(1-(4-methyl-benzyl)-6-oxo-piperidin-2-yl)-7-chloro-3H-quinazolin-4-one.

Utility, Testing and Administration

General Utility

The compounds of the invention find use in a variety of applications, including as therapeutic active agents, in the practice of the methods of treatment, in compositions, particularly pharmaceutical formulations and in methods for the manufacture of pharmaceutical formulations, and as intermediates in the synthesis of such therapeutic active agents.

As will be appreciated by those in the art, mitosis can be altered in a variety of ways; that is, one can affect mitosis either by increasing, decreasing or otherwise interfering with the activity of a component in the mitotic pathway. Stated differently, mitosis can be affected (e.g., disrupted) by disturbing equilibrium, either by inhibiting or activating certain mitotic components. Similar approaches can be used to alter meiosis.

The compounds of the invention can be used to inhibit mitotic spindle formation. Such inhibition may take the form of lessening a mitotic kinesin's organization of microtubules into bipolar structures, increasing or decreasing spindle pole separation, and/or inducing mitotic spindle dysfunction. In particular, the compounds of the invention are useful to bind to and/or inhibit the activity of a mitotic kinesin, KSP, especially human KSP, although KSP kinesins from other organisms may also be used. Also included within the definition of the term "KSP" for these purposes are variants and/or fragments of KSP. See, U.S. Pat. No. 6,437,115. While other mitotic kinesins may be used in the present invention, the compounds of the invention have been shown to have specificity for KSP. Contacting a compound of the invention with a KSP kinesin, particularly human KSP kinesin, can lead to diminished KSP-mediated ATP hydrolysis activity and/or diminished KSP-mediated mitotic spindle formation activity. Meiotic spindles can be similarly disrupted.

In another embodiment, the compounds of the invention can be used to modulate one or more other human mitotic kinesins, in addition to inhibiting KSP, including: HSET (see, U.S. Pat. No. 6,361,993); MCAK (see, U.S. Pat. No. 6,331,424); CENP-E (see, PCT Publication No. WO 99/13061); Kif4 (see, U.S. Pat. No. 6,440,684); MKLP1 (see, U.S. Pat. No. 6,448,025); Kif15 (see, U.S. Pat. No. 6,355,466); Kid (see, U.S. Pat. No. 6,387,644); Mpp1, CMKrp, Kinl-3 (see, U.S. Pat. No. 6,461,855); Kip3a (see, PCT Publication No. WO 01/96593); Kip3d (see, U.S. Pat. No. 6,492,151); and RabK6.

Therapeutic uses facilitated by the mitotic kinesin-inhibitory activity of the compounds of the present invention include the treatment of disorders associated with cell proliferation. Particular disease states that can be treated by the methods, pharmaceutical formulations, and compounds provided herein include, but are not limited to, cancer (further discussed below), autoimmune disease, arthritis, graft rejection, inflammatory bowel disease, proliferation induced after medical procedures, including, but not limited to, surgery, angioplasty, and the like. In one embodiment, the invention includes application to cells or individuals afflicted or impending afflication with any one of these disorders or states.

The compounds, pharmaceutical formulations and methods provided herein are particularly deemed useful for the treatment of cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells, including cells afflicted by any one of the above-identified conditions.

Another useful aspect of the invention is a kit having a compound, salt or solvate of Formula I or II and a package insert or other labeling including directions treating a cellular proliferative disease by administering an effective amount of the compound, salt or solvate. The compound, salt or solvate of Formula I or II in the kits of the invention is particularly provided as one or more doses for a course of treatment for a cellular proliferative disease, each dose being a pharmaceutical formulation including a pharmaceutically accepted excipient and a compound, salt or solvate of Formula I or II.

Testing

To assay activity, generally, either KSP or a compound according to the invention is non-diffusably bound to an insoluble support having isolated sample receiving areas. The insoluble support can be made of any material to which the compounds can be bound, is readily separated from soluble material, and is otherwise compatible with the overall method of screening. The surface of such supports can be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the compound is not crucial so long as it is compatible with the reagents and overall methods of the invention, maintains the activity of the compound and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas can then be blocked through incubation with bovine serum albumin (BSA), casein or other innocuous protein or other moiety.

The compounds of the invention can be used on their own to modulate the activity of a mitotic kinesin, particularly KSP. In this embodiment, a compound of the invention is combined with KSP and the activity of KSP is assayed. Measurable kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. [See e.g., Hall, et al. (1996), Biophys. J., 71: 3467–3476, Turner et al., 1996, AnaL Biochem. 242 (1):20–5; Gittes et al., 1996, Biophys. J. 70(I): 418–29; Shirakawa et al., 1995, J. Exp. BioL 198:1809–15; Winkelmann et al., 1995, Biophys. J. 68: 2444–53; Winkelmann et al., 1995, Biophys. J. 68: 72S.]

Methods known in the art for determining ATPase hydrolysis activity also can be used. Solution based assays are particularly suitable (see, U.S. Pat. No. 6,410,254); alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μL of reaction is quenched in 90 μL of cold 0.3 M PCA. Phosphate standards are used so data can be converted to mM inorganic phosphate released. When all reactions and standards have been quenched in PCA, 100 μL of malachite green reagent is added to the relevant wells in e.g., a microtiter plate. The mixture is developed for 10–15 minutes and the plate is read at an absorbance of 650 nm. When phosphate standards are used, absorbance readings can be converted to mM $P_i$ and plotted over time. Additionally, ATPase assays known in the art include the luciferase assay.

ATPase activity of kinesin motor domains also can be used to monitor the effects of modulating agents. In one embodiment ATPase assays of kinesin are performed in the absence of microtubules. In another embodiment, the ATPase assays are performed in the presence of microtubules. Different types of modulating agents can be detected in the above assays. In one particular embodiment, the effect of a modulating agent is independent of the concentration of microtubules and ATP. In another embodiment, the effect of the agents on kinesin ATPase can be decreased by increasing the concentrations of ATP, microtubules or both. In yet another embodiment, the effect of the modulating agent is increased by increasing concentrations of ATP, microtubules or both.

Agents that modulate the biochemical activity of KSP in vitro may then be screened in vivo. Methods for testing such agents in vivo include assays of cell cycle distribution, cell viability, or the presence, morphology, activity, distribution or amount of mitotic spindles. Methods for monitoring cell cycle distribution of a cell population, for example, by flow cytometry, are well known to those skilled in the art, as are methods for determining cell viability. See, for example, WO 01/31335, entitled "Methods of Screening for Modulators of Cell Proliferation and Methods of Diagnosing Cell Proliferation States."

In addition to the assays described above, microscopic methods for monitoring spindle formation and malformation are well known to those of skill in the art (see, e.g., Whitehead and Rattner (1998), J. Cell Sci. 111:2551–61; Galgio et al, (1996) J. Cell Biol., 135:399–414).

The compounds of the invention inhibit KSP kinesin. One measure of inhibition, $IC_{50}$, is defined as the concentration of the compound at which the activity of KSP is decreased by fifty percent. Particularly suitable compounds have $IC_{50}$'s of less than about 1 mM, with more particularly suitable compounds having $IC_{50}$'s of less than about 100 μM. $IC_{50}$'s of less than about 10 nM can be attained by certain compounds of the invention, and the pharmaceutically acceptable salts and solvates thereof, it being appreciated that a smaller $IC_{50}$ is generally considered advantageous. Measurement of $IC_{50}$ is done using an ATPase assay.

Another measure of inhibition is $K_i$. For compounds with $IC_{50}$'s less than 1 μM, the $K_i$ or $K_d$ is defined as the dissociation rate constant for the interaction of the test compound with KSP. Particularly suitable compounds have $K_i$'s of less than about 100 μM, more particularly suitable compounds having $K_i$'s of less than about 10 μM. $K_i$'s of less than about 10 nM can be attained by certain compounds of the invention, and the pharmaceutically acceptable salts and solvates thereof, it being appreciated that a smaller $K_i$ is generally considered advantageous. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max} E_0 \left[ 1 - \frac{(E_0 + I_0 + Kd) - \sqrt{(E_0 + I_0 + Kd)^2 - 4E_0 I_0}}{2E_0} \right]$$

Where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 μM, and hydroxyurea is 500 μM (data provided by National Cancer Institute, Developmental Therapeutic Program, http://dtp.nci.nih.gov/). Therefore, compounds that inhibit cellular proliferation at virtually any concentration may be useful. Particularly suitable compounds have $GI_{50}$'s of less than about 1 mM, with more particularly suitable compounds having a $GI_{50}$ of less than about 10 μM. $GI_{50}$'s of less than about 10 nM can be attained by certain compounds of the invention, and the pharmaceutically acceptable salts and solvates thereof, it being appreciated that a smaller $GI_{50}$ is generally considered advantageous. Measurement of $GI_{50}$ is done using a cell proliferation assay.

Testing for growth inhibition using cell lines (such as MCF-7/ADR-RES and HCT1 5) that express P-glycoprotein (also known as Multi-drug Resistance, or $MDR^+$), which conveys resistance to other chemotherapeutic drugs, such as pacilitaxel, can identify anti-mitotic agents that inhibit cell proliferation and are not subject to resistance by overexpression of $MDR^+$ by drug-resistant tumor lines.

In vitro potency of small molecule inhibitors is determined by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

To employ the compounds of the invention in a method of screening for compounds that bind to KSP kinesin, the KSP is bound to a support, and a compound or composition of the invention is added to the assay. Alternatively, a composition of a compound of the invention bound to a solid support can be made, and KSP added to the assay. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a particular embodiment, the compound of the invention is labeled, for example, with a fluorescent or radioactive moiety and binding determined directly. For example, this may be done by attaching all or a portion of KSP to a solid support, adding a labeled compound (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}I$, or with fluorophores. Alternatively, more than one component may be labeled with different labels; using $^{125}I$ for the proteins, for example, and a fluorophor for the anti-mitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that protein, for example, polymer structures such as microtubules, and energy sources such as ATP. Particular embodiments of assays herein include candidate agents that do not bind the cellular proliferation protein in its endogenous native state termed herein as "exogenous" agents. In another particular embodiment, exogenous agents further exclude antibodies to KSP.

Candidate agents can encompass numerous chemical classes, though typically they are organic molecules, particularly small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, especially at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays can be done by combining KSP and a drug candidate in a first sample. A second sample may be made combining a compound of the invention, KSP and a drug candidate. This may be performed in either the presence or absence of microtubules. The binding of the drug candidate is determined for both samples, and a change or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a particularly suitable embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations can be performed at any temperature that facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a particularly suitable embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the compound, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Formulation and Administration

The compounds, pharmaceutically acceptable salts and solvates of Formula I and II are administered at a therapeutically effective dosage, e.g., a dosage sufficient to provide treatment for the disease states previously described. Human dosage levels are typically determined by escalating dose ranging studies conducted in accordance with current Good Clinical Practice, FDA and local guidelines. The amount of active compound administered will, of course, be dependent on the subject and disease state being treated, the severity of the affliction, the manner and schedule of administration and the judgment of the prescribing physician.

The administration of the compounds and pharmaceutical formulations of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical formulations include a compound of Formula I or II or a pharmaceutically acceptable salt or solvate thereof, and one or more pharmaceutically acceptable excipients. As is known in the art, pharmaceutical excipients are secondary ingredients that function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995). The concentration of a therapeutically active agent in a formulation can vary widely, from about 0.1 to 99.9 wt. %, depending on the nature of the formulation.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

- alcohol, e.g., 5% alcohol (e.g., in dextrose and water ("D/W") or D/W in normal saline solution ("NSS"), including in 5% dextrose and water ("D5A/W"), or D5/W in NSS);
- synthetic amino acid such as Aminosyn, FreAmine, Travasol, e.g., 3.5 or 7; 8.5; 3.5, 5.5 or 8.5% respectively;
- ammonium chloride e.g., 2.14%;
- dextran 40, in NSS e.g., 10% or in D5/W e.g., 10%;
- dextran 70, in NSS e.g., 6% or in D5/W e.g., 6%;
- dextrose (glucose, D5/W) e.g., 2.5–50%;
- dextrose and sodium chloride e.g., 5–20% dextrose and 0.22–0.9% NaCl;
- lactated Ringer's (Hartmann's) e.g., NaCl 0.6%, KCl 0.03%, $CaCl_2$ 0.02%;
- lactate 0.3%;
- mannitol e.g., 5%, optionally in combination with dextrose e.g., 10% or NaCl e.g., 15 or 20%;
- multiple electrolyte solutions with varying combinations of electrolytes, dextrose, fructose, invert sugar Ringer's e.g., NaCl 0.86%, KCl 0.03%, $CaCl_2$ 0.033%;
- sodium bicarbonate e.g., 5%;
- sodium chloride e.g., 0.45, 0.9, 3, or 5%;
- sodium lactate e.g., 1/6 M; and
- sterile water for injection The pH of such IV fluids may vary, and will typically be from 3.5 to 8 as known in the art.

The compounds, pharmaceutically acceptable salts and solvates of the invention can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

N-(3-amino-propyl)-N-[1-(3-benzyl-4-oxo-3,4-dihydro-pyrido[2,3-d]pyrimidin-2-yl)-2-methyl-propyl]-4-methyl-benzamide 1A. Formula 106 where $R^1$, $R^2$, $R^4$, $R^6$, $R^7$, $R^8$ and $R^9$ are H; $R^3$ is Chloro; and $R^5$ is Benzyl: To a solution of Formula 101, 4-tert-butoxycarbonylamino-2-(9H-fluoren-9-yl-methoxycarbonylamino)-butyric acid (1.00 g, 2.27 mmol) in 20 mL of anhydrous THF was added anhydrous N-methylmorpholine (274 μL, 2.50 mmol). After the mixture was stirred in an ice-bath for 1 minute, isobutyl chloroformate (324 μL, 2.50 mmol) was added dropwise over 15 minutes at 0° C. The mixture was stirred in the ice-bath for 1 hour, after which 4-chloro-anthranilic acid (389 mg, 2.27 mmol) in 2 mL of THF was added, affording the corresponding compound of Formula 103, 2-[4-tert-butyxycarbonylamino-2-(9H-fluoren-9-ylmethoxy-carbonylamino)-butyrylamino]-4-chloro-benzoic acid, following 2 hours of additional stirring at 0° C. To the stirring compound of Formula 103, anhydrous N-methylmorpholine (274 μL, 2.50 mmol) was added and the mixture stirred overnight while slowly warming to room temperature. The mixture was then cooled to 0° C. and treated with anhydrous N-methylmorpholine (274 μL, 2.50 mmol) and isobutyl chloroformate (324 μL, 2.50 mmol). This was followed by addition of benzylamine (992 μL, 3.92 mmol) in four equal portions at room temperature. Once the starting material was consumed, the solvents were evaporated and the residue partitioned between DCM and saturated sodium bicarbonate. The organic layer was dried over sodium sulfate and the solvent was evaporated, affording a mixture of the corresponding compounds of Formula 104 and Formula 105, [1-(2-benzyl-carbamoyl-5-chloro-phenyl-carbamoyl)-3-tert-butoxycarbonylamino-propyl]-carbamic acid 9H-fluoren-9-ylmethyl ester and [1-(3-benzyl-7-chloro-4-oxo-c,4–3,4-dihydroquinazolin-2-yl)-3-tert-butoxycarbonyl-amino-propyl]-carbamic acid 9H-fluoren-9-ylmethyl ester, respectively (about 6:1 by LCMS) which was dried under vacuum and then treated with lithium hydroxide monohydrate (95 mg, 2.27 mmol) in 60 mL of 1,4-dioxane/ethylene glycol (2/1) under reflux for 5 hours. The reaction solution was poured into 200 mL of water and the product extracted with DCM. After drying the organic layers over sodium sulfate, the solvent was evaporated and the crude product purified by flash silica gel chromatography (stepwise gradient 1:4, 1:2, 1:1, 2:1, 4:1 with ethyl acetate:hexanes as eluent) to give the corresponding product of Formula 106, [3-amino-3-(3-benzyl-7-chloro-4-oxo-3,4-dihydro-quinazolin-2-yl)-propyl]-carbamic acid tert-butyl ester (700 mg, 70%).

1B. Formula 107 where $R^1$, $R^2$, $R^4$, $R^6$, $R^7$, $R^8$ and $R^9$ are H: $R^3$ is Chloro; $R^5$ is Benzyl; and $R^{10}$ is p-Methyl-benzyl: To a solution of [3-amino-3-(3-benzyl-7-chloro-4-oxo-3,4-dihydro-quinazolin-2-yl)-propyl]-carbamic acid tert-butyl ester (700 mg, 1.58 mmol) and DIEA (275 μL, 2.37 mmol) in 50 mL of DCM was added p-tolualdehyde (188 μL, 1.58 mmol). The mixture was stirred for 1 hour, after which sodium triacetoxyborohydride (500 mg, 2.37 mmol) was added. After stirring an additional 3 hours, the mixture was washed with saturated sodium bicarbonate solution, dried over sodium sulfate. The solvents were evaporated to dryness and the residue was purified by flash silica gel chromatography (stepwise gradient 1:4, 1:2, 1:1, 2:1, 4:1 with ethyl acetate:hexanes as eluent) to give the corresponding, pure compound of Formula 107, [3-(3-benzyl-7-chloro-4-oxo-3,4-dihydro-quinazolin-2-yl)-3-(4-methyl-benzylamino)-propyl]-carbamic acid tert-butyl ester (760 mg, 88%).

1C. Formula 108 where $R^1$, $R^2$, $R^4$, $R^6$, $R^7$, $R^8$ and $R^9$ are H; $R^3$ is Chloro; $R^5$ is Benzyl; $R^{10}$ is p-Methyl-benzyl; and R''' is NHBoc-Ethyl: [3-(3-Benzyl-7-chloro-4-oxo-3,4-dihydro-quinazolin-2-yl)-3-(4-methyl-benzylamino)-propyl]-carbamic acid tert-butyl ester (360 mg, 0.658 mmol) was dissolved in 10 mL of TFA/$H_2O$ (95/5) solution and stirred for 30 minutes. The solvents were evaporated and the residue partitioned between DCM and saturated sodium bicarbonate solution. The organic layer was dried over sodium sulfate and the solvents evaporated to dryness. The resulting residue, DIEA (168 μL, 0.966 mmol), tert-butyl N-(2-oxoethyl) carbamate (122 mg, 0.767 mmol) and sodium triacetoxyborohydride (318 mg, 0.966 mmol) were mixed in 50 mL of DCM and stirred for 1 hour. The solution was then washed with 100 mL of saturated sodium bicarbonate solution and dried over sodium sulfate. The solvent was evaporated to dryness to give the corresponding compound of Formula 108, {2-[3-(3-benzyl-7-chloro-4-oxo-3,4-dihydro-quinazolin-2-yl)-3-(4-methyl-benzylamino)-propylamino]-ethyl}-carbamic acid tert-butyl ester (380 mg, 98%).

1D. Formula I where $R^1$, $R^2$, $R^4$, $R^6$, $R^7$, $R^8$ and $R^9$ are H; $R^3$ is Chloro; $R^5$ is Benzyl; $R^{10}$ is p-Methyl-benzyl; and V is NR' where R''' is Amino-ethyl: To a solution of crude {2-[3-(3-benzyl-7-chloro-4-oxo-3,4-dihydro-quinazolin-2-yl)-3-(4-methyl-benzylamino)-propylamino]-ethyl}-carbamic acid tert-butyl ester (380 mg, 0.644 mmol) and DIEA (167 μL, 0.966 mmol) in 50 mL of DCM was added carbonyldiimidazole (157 mg, 0.966 mmol) and the reaction mixture stirred for 1 hour. The solvent was evaporated and the residue purified by flash silica gel chromatography (stepwise gradient 1:4, 1:2, 1:1, 2:1, 4:1 with ethyl acetate: hexanes as eluent) to give the corresponding, pure R'''-Boc-protected precursor to Formula I (250 mg, 63%). This product (250 mg, 0.405 mmol) was dissolved in 10 mL of TFA/$H_2O$ (95/5) solution, stirred for 1 hour, and then evaporated to dryness. The residue was partitioned between DCM and saturated sodium bicarbonate, the organic layer was dried over sodium sulfate, and the solvents evaporated to dryness. The residue was dried under vacuum for a few hours to give the desired product of Formula I, 2-[-1-(2-amino-ethyl)-3-(4-methyl-benzyl)-2-oxo-hexahydro-pyrimidin-4-yl]-3-benzyl-7-chloro-3H-quinazolin-4-one (188 mg, 90%).

Example 2

Other Compounds of Formulae I and II

2A. Formula I where $R^1$, $R^2$, $R^4$, $R^6$, $R^8$ and $R^9$ are H; $R^3$ is Chloro; $R^5$ is Benzyl; $R^7$ is i-Propyl; $R^{10}$ is p-Methyl-benzyl; and V is NR' where R''' is Amino-ethyl: By following the procedure described in Example 1 and substituting 4-tert-butoxycarbonylamino-2-(9H-fluoren-9-ylmethoxycarbonylamino)-butyric acid with 3-(tert-butoxycarbonylamino-methyl)-2-(9H-fluoren-9-ylmethoxycarbonylamino)-4-methyl-pentanoic acid, there is obtained 2-[-1-(2-amino-ethyl)-5-isopropyl-3-(4-methyl-benzyl)-2-oxo-hexahydro-pyrimidin-4-yl]-3-benzyl-7-chloro-3H-quinazolin-4-one.

2B. Formula I where $R^1$, $R^4$, $R^6$, $R^7$, $R^8$ and $R^9$ are H; $R^2$ and $R^3$ are Methoxy; $R^5$ is Benzyl; $R^{10}$ is p-Methyl-benzyl; and V is NR' where R''' is Amino-ethyl: By following the procedure described in Example 1 and substituting 4-chloro-anthranilic acid with 2-amino-4,5-dimethoxy benzoic acid, there is obtained 2-[-1-(2-amino-ethyl)-3-(4-methyl-benzyl)-2-oxo-hexahydro-pyrimidin-4-yl]-3-benzyl-6,7-dimethoxy-3H-quinazolin-4-one.

2C. Formula I where $R^1$, $R^2$, $R^4$, $R^6$, $R^7$, $R^8$ and $R^9$ are H; $R^3$ is Methoxy; $R^5$ is Benzyl; $R^{10}$ is p-Methyl-benzyl; and V is NR''' where R''' is Isopropyl: By following the procedure described in Example 1 and substituting tert-butyl N-(2-oxoethyl) carbamate with 2-methylpriopionaldehyde, there is obtained 2-[-1-isopropyl-3-(4-methyl-benzyl)-2-oxo-hexahydro-pyrimidin-4-yl]-3-benzyl-7-chloro-3H-quinazolin-4-one.

2D. Formula II where T is Methylene; W, X, Y and Z are —C=; $R^1$, $R^2$, $R^4$, $R^6$, $R^8$ and $R^9$ are H; $R^3$ is Chloro; $R^5$ is Benzyl; $R^7$ is i-Propyl; $R^{10}$ is p-Methyl-benzyl; and V is NR' where R''' is Amino-ethyl: By following the procedure described in Example 1 and substituting 4-tert-butoxycarbonylamino-2-(9H-fluoren-9-ylmethoxycarbonylamino)-butyric acid with 4-(tert-butoxycarbonylamino-methyl)-3-[(9H-fluoren-9-yl)-methoxycarbonyl-amino]-5-methyl-hexanoic acid, there is obtained 2-[-1-(2-amino-ethyl)-5-isopropyl-3-(4-methyl-benzyl)-2-oxo-hexahydro-pyrimidin-4-ylmethyl]-3-benzyl-7-chloro-3H-quinazolin-4-one.

2E. Formula II where T is Carboxyethylene; W, X, Y and Z are —C=; $R^1$, $R^2$, $R^4$, $R^6$, $R^8$ and $R^9$ are H; $R^3$ is Chloro; $R^5$ is Benzyl; $R^{10}$ is p-Methyl-benzyl; and V is NR' where R''' is Isopropyl: By following the procedure described in Example 1, substituting in 4-tert-butoxycarbonylamino-2-(9H-fluoren-9-ylmethoxycarbonylamino)-butyric acid with 6-(tert-butoxycarbonylamino)-4-[(9H-fluoren-9-yl)-methoxycarbonyl-amino]-3-oxo-hexanoic acid in Example 1A, and substituting tert-butyl N-(2-oxoethyl) carbamate with 2-methyl-propionaldehyde in Example 1C, there is obtained 3-benzyl-7-chloro-2-{2-[1-isopropyl-3-(4-methyl-benzyl)-2-oxo-hexahydro-pyrimidin-4-yl]-2-oxo-ethyl}-3H-quinazolin-4-one.

2F. Formula II where T is Carboxyethylene: W and Y are —C=: X and Z are —N=; $R^1$, $R^2$, $R^4$, $R^6$, $R^8$ and $R^9$ are H: $R^3$ is Chloro; $R^5$ is Benzyl; $R^{10}$ is p-Methyl-benzyl; and V is NR' where R''' is Isopropyl: By following the procedure described in Example 2E and additionally substituting 4-chloro-anthranilic acid with 4-amino-pyridine-5-carboxylic acid in Example 1 A, there is obtained 3-benzyl-2-{2-[1-isopropyl-3-(4-methyl-benzyl)-2-oxo-hexahydro-pyrimidin-4-yl]-2-oxo-ethyl}-3H-pyrimido[4,5-d]pyrimidin-4-one.

Example 3

3-Benzyl-2-(1-benzyl-6-oxo-piperidin-2-yl)-7-chloro-3H-quinazolin-4-one

3A. Formula 203 where R', R'', $R^6$, $R^7$, $R^8$ and $R^9$ are H; and $R^{10}$ is Benzyl: DL-2-Aminoadipic acid hydrate (2 g, 11 mmol) was dissolved in 2 M NaOH (11 mL, 22 mmol). Benzaldehyde (1.4 mL, 11 mmol) was dissolved in 3.0 mL of ethanol and this solution was added to the first solution. After 10 minutes the mixture was cooled to 0° C. and sodium borohydride (0.13 g, 3.3 mmol) was added. After 1 hour, LCMS analysis showed the reaction to be complete. The solution was extracted 3 times with 20 mL portions of ether, cooled to 0° C., acidified to pH 2 with conc. HCl, and the resulting precipitate was filtered to afford a damp white solid. The solid was washed once with a minimum amount of acetonitrile (~1 mL) and three times with ether. The crude solid was dissolved in 55 mL ethanol and the solution was boiled overnight. The solution was evaporated to provide 1.22 g (47% yield for 2 steps) of the lactam product of Formula 203, 1-benzyl-6-oxo-piperidine-2-carboxylic acid, which was carried on without further purification.

3B. Formula 204 where R', R'', $R^1$, $R^2$, $R^4$, $R^6$, $R^7$, $R^8$ and $R^9$ are H; $R^3$ is Chloro; and $R^{10}$ is Benzyl: 1-Benzyl-6-oxo-piperidine-2-carboxylic acid (1 g, 4.3 mmol) and DIEA (0.75 mL, 4.3 mmol) were dissolved in 20 mL of dichloromethane and cooled to 0° C. Isobutylchloroformate (0.59 mL, 4.3 mmol) was added and the mixture was stirred for 20 minutes. More DIEA (1.5 mL, 8.6 mmol) was added, followed by 4-chloroanthranilic acid (0.77 g, 4.5 mmol), and the mixture was allowed to warm to room temperature overnight. The mixture was washed with 1 M HCl and brine, dried over MgSO$_4$, and evaporated to provide a yellow oily solid. This material was dissolved in 3 mL of 2 M NaOH, washed twice with ether, cooled to 0° C., and acidified with conc. HCl. A pale yellow oil formed, which solidified upon standing. This material was filtered and dried under vacuum to provide 0.57 g (34% yield) of the benzoic acid of Formula 204, 2-[(1-benzyl-6-oxo-piperidine-2-carbonyl)-amino]-4-chloro-benzoic acid, which was carried on without further purification.

3C. Formula I where $R^1$, $R^2$, $R^4$, $R^6$, $R^7$, $R^8$ and $R^9$ are H; $R^3$ is Chloro; $R^5$ is Benzyl, $R^{10}$ is Benzyl; and V is CR'R" where R' and R" are H: To a solution of 2-[(1-benzyl-6-oxo-piperidine-2-carbonyl)-amino]-4-chloro-benzoic acid (165 mg, 0.427 mmol) in 5 mL of DMF was added EDC (245 mg, 1.28 mmol) and the mixture stirred at room temperature. After 1 hour, benzylamine (140 μL, 1.28 mmol) was added, and the reaction mixture was stirred at room temperature for an additional 3 hours. After evaporating the solvents, the residue was dissolved in 100 mL of DCM, and washed with saturated sodium bicarbonate and brine. The organic layer was dried over sodium sulfate and filtered. The solvent was removed to afford crude 1-benzyl-6-oxo-piperidine-2-carboxylic acid (2-benzylcarbamoyl-5-chloro-phenyl)-amide, a compound of Formula 402. This was dried under vacuum and then added to a mixture of 10 mL of ethylene glycol and sodium hydroxide (17 mg, 0.425 mmol), followed by stirring at 130° C. for two days with monitoring by LC-MS. The mixture was then poured into 100 mL of water. After extraction with DCM, the resulting crude product was purified over silica gel (stepwise gradient 1:4, 1:2, 1:1, 2:1, 4:1 with ethyl acetate:hexanes as eluent) to give the desired pure product of Formula I, 3-benzyl-2-(1-benzyl-6-oxo-piperidin-2-yl)-7-chloro-3H-quinazolin-4-one (20 mg, 10%).

Example 4

Other Compounds of Formulae I and II

4A. Varying T, V and $R^6$ to $R^9$ By following the procedure described in Example 3 and substituting DL-2-aminoadipic acid hydrate with the following:
  2-amino-pentanedioic acid;
  4-amino-2,2-dimethyl-pentanedioic acid;
  2-amino-3-methyl-hexanedioic acid;
  2-amino-4-isopropyl-hexanedioic acid;
  2-amino-3,4-dihydroxy-hexanedioic acid;
  5-amino-2,3-diethoxy-hexanedioic acid;
  4-amino-octanedioic acid; and
  5-amino-6-carboxymethoxy-hexanoic acid, there are obtained the following respective compounds:
  3-benzyl-2-(1-benzyl-5-oxo-pyrrolidin-2-yl)-7-chloro-3H-quinazolin-4-one;
  3-benzyl-2-(1-benzyl-4,4-dimethyl-5-oxo-pyrrolidin-2-yl)-7-chloro-3H-quinazolin-4-one;
  3-benzyl-2-(1-benzyl-3-methyl-6-oxo-piperidin-2-yl)-7-chloro-3H-quinazolin-4-one;
  3-benzyl-2-(1-benzyl-4-isopropyl-6-oxo-piperidin-2-yl)-7-chloro-3H-quinazolin-4-one;
  3-benzyl-2-(1-benzyl-3,4-dihydroxy-6-oxo-piperidin-2-yl)-7-chloro-3H-quinazolin-4-one;
  3-benzyl-2-(1-benzyl-4,5-diethoxy-6-oxo-piperidin-2-y)-7-chloro-3H-quinazolin-4-one;
  3-benzyl-2-[3-(1-benzyl-5-oxo-pyrrolidin-2-yl)-propyl]-7-chloro-3H-quinazolin-4-one;
  3-benzyl-2-(1-benzyl-6-oxo-piperidin-2-ylmethoxymethyl)-7-chloro-3H-quinazolin-4-one.

4B. Varying $R^{10}$ By following the procedure described in Examples 3 and 4A, and substituting benzaldehyde with 4-methyl-benzaldehyde, there are obtained:
  3-benzyl-2-[1-(4-methyl-benzyl)-5-oxo-pyrrolidin-2-yl]-7-chloro-3H-quinazolin-4-one;
  3-benzyl-2-[4,4-dimethyl-1-(4-methyl-benzyl)-5-oxo-pyrrolidin-2-yl]-7-chloro-3H-quinazolin-4-one;
  3-benzyl-2-[3-methyl-1-(4-methyl-benzyl)-6-oxo-piperidin-2-yl]-7-chloro-3H-quinazolin-4-one;
  3-benzyl-2-[4-isopropyl-1-(4-methyl-benzyl)-6-oxo-piperidin-2-yl]-7-chloro-3H-quinazolin-4-one;
  3-benzyl-2-[3,4-dihydroxy-1-(4-methyl-benzyl)-6-oxo-piperidin-2-yl]-7-chloro-3H-quinazolin-4-one;
  3-benzyl-2-[4,5-diethoxy-1-(4-methyl-benzyl)-6-oxo-piperidin-2-yl]-7-chloro-3H-quinazolin-4-one;
  3-benzyl-2-{3-[1-(4-methyl-benzyl)-5-oxo-pyrrolidin-2-yl]-propyl}-7-chloro-3H-quinazolin-4-one; and
  3-benzyl-2-[1-(4-methyl-benzyl)-6-oxo-piperidin-2-ylmethoxymethyl]-7-chloro-3H-quinazolin-4-one;

4C. Varying T, V, and R' or $R^9$ By following the procedure described in Example 3, substituting DL-2-aminoadipic acid hydrate with the following:
  2-amino-4-(2-tert-butoxycarbonylamino-ethyl)-pentanedioic acid;
  2-amino-5-(2-tert-butoxycarbonylamino-ethyl)-hexanedioic acid; and
  5-amino-2-(2-tert-butoxycarbonylamino-ethyl)-6-(tert-butoxycarbonyl-carboxymethyl-amino)-hexanoic acid, and de-protecting the product thus-obtained (for example, as described in the second part of Example 1D), there are obtained the following respective compounds:
  3-benzyl-2-[4-(2-amino-ethyl)-1-benzyl-5-oxo-pyrrolidin-2-yl]-7-chloro-3H-quinazolin-4-one;
  3-benzyl-2-[5-(2-amino-ethyl)-1-benzyl-6-oxo-piperidin-2-yl]-7-chloro-3H-quinazolin-4-one; and
  2-({[5-(2-amino-ethyl)-1-benzyl-6-oxo-piperidin-2-ylmethyl]-amino}-methyl)-3-benzyl-7-chloro-3H-quinazolin-4-one.

4D. Varying T, V, $R^1$, $R^9$ and $R^{10}$ By following the procedure described in Example 4C and substituting benzaldehyde with (2-oxo-ethyl)-carbamic acid tert-butyl ester, there are obtained:
  3-benzyl-2-[1,4-bis-(2-amino-ethyl)-5-oxo-pyrrolidin-2-yl]-7-chloro-3H-quinazolin-4-one;
  3-benzyl-2-[1,5-bis-(2-amino-ethyl)-6-oxo-piperidin-2-yl]-7-chloro-3H-quinazolin-4-one; and
  3-benzyl-2-({[1,5-bis-(2-amino-ethyl)-6-oxo-piperidin-2-ylmethyl]-amino}-methyl)-7-chloro-3H-quinazolin-4-one.

4E. Varying T, V, R' to $R^4$, $R^6$ to $R^9$ and W, X, Y and Z By following the procedure as described with 2-amino-pentanedioic acid, 4-amino-2,2-dimethyl-pentanedioic acid and 2-amino-3-methyl-hexanedioic acid in Example 4A, and additionally substituting 4-chloroanthranilic acid (from Example 3B) with the following:
  3-amino-pyrazine-2-carboxylic acid;
  3-amino-1,4-dihydro-pyridine-2-carboxylic acid;
  2-amino-cyclopent-1-enecarboxylic acid;
  4-amino-2,5-dihydro-furan-3-carboxylic acid; and
  3-amino-1H-pyrrole-2-carboxylic acid, there are obtained the following respective compounds:

3-benzyl-2-(1-benzyl-5-oxo-pyrrolidin-2-yl)-3H-pteridin-4-one;

3-benzyl-2-(1-benzyl-5-oxo-pyrrolidin-2-yl)-5,8-dihydro-3H-pyrido[3,2-d]pyrimidin-4-one;

3-benzyl-2-(1-benzyl-5-oxo-pyrrolidin-2-yl)-3,5,6,7-tetrahydro-cyclopentapyrimidin-4-one;

3-benzyl-2-(1-benzyl-5-oxo-pyrrolidin-2-yl]-5,7-dihydro-3H-furo[3,4-d]pyrimidin-4-one;

3-benzyl-2-(1-benzyl-5-oxo-pyrrolidin-2-yl]-3,7-dihydro-pyrrolo[3,2-d]pyrimidin-4-one;

3-benzyl-2-(1-benzyl-4,4-dimethyl-5-oxo-pyrrolidin-2-yl)-3H-pteridin-4-one;

3-benzyl-2-(1-benzyl-4,4-dimethyl-5-oxo-pyrrolidin-2-yl)-5,8-dihydro-3H-pyrido[3,2-d]pyrimidin-4-one;

3-benzyl-2-(1-benzyl-4,4-dimethyl-5-oxo-pyrrolidin-2-yl)-3,5,6,7-tetrahydro-cyclopentapyrimidin-4-one;

3-benzyl-2-(1-benzyl-4,4-dimethyl-5-oxo-pyrrolidin-2-yl]-5,7-dihydro-3H-furo[3,4-d]pyrimidin-4-one;

3-benzyl-2-(1-benzyl-4,4-dimethyl-5-oxo-pyrrolidin-2-yl]-3,7-dihydro-pyrrolo[3,2-d]pyrimidin-4-one;

3-benzyl-2-(1-benzyl-3-methyl-6-oxo-piperidin-2-yl)-3H-pteridin-4-one;

3-benzyl-2-(1-benzyl-3-methyl-6-oxo-piperidin-2-yl)-5,8-dihydro-3H-pyrido[3,2-d]pyrimidin-4-one;

3-benzyl-2-(1-benzyl-3-methyl-6-oxo-piperidin-2-yl)-3,5,6,7-tetrahydro-cyclopentapyrimidin-4-one;

3-benzyl-2-(1-benzyl-3-methyl-6-oxo-piperidin-2-yl]-5,7-dihydro-3H-furo[3,4-d]pyrimidin-4-one; and 3-benzyl-2-(1-benzyl-3-methyl-6-oxo-piperidin-2-yl]-3,7-dihydro-pyrrolo[3,2-d]pyrimidin-4-one.

Example 5

3-Benzyl-7-chloro-2-[3-(4-methyl-benzyl)-2-oxo-hexahydro-pyrimidin-4-yl]-3H-quinazolin-4-one 5A. Formula 302 where $R^6$, $R^7$, $R^8$ and $R^9$ are H: DL-2,4-Diaminobutyric acid (4.9 g, 26 mmol) and sodium bicarbonate (6.5 g, 77 mmol) was dissolved in 25 mL of water. Copper sulfate (3.2 g, 13 mmol) was dissolved in 25 mL of water and this solution was added to the first solution. To this mixture was added a solution of di-(tert-butyl) pyrocarbonate (7.3 g, 33.5 mmol) dissolved in 32 mL of acetone. After stirring for 24 hours, methanol was added to the mixture and stirring was continued for another 18 hours. The resulting light blue precipitate was filtered, washed twice with water, and dried under vacuum to provide 3.3 g (51%) of the mono-Boc-protected copper complex of diaminobutyric acid. This copper complex (3.3 g, 6.7 mmol) was suspended in 300 mL of water and quinolinol (2.5 g, 17 mmol) was added. After 5 hours, the suspension was filtered off and the liquid was evaporated to provide approximately 3.5 g of a wet yellow solid. This material was dissolved in 200 mL of 30% methanol in benzene. To this solution was added dropwise (trimethylsilyl)diazomethane (2.0 M in hexanes, approximately 12 mL, approximately 24 mmol) until a deep yellow color persisted and bubbling ceased. This solution was stirred for 1 hour. Acetic acid was added dropwise until the deep yellow color was discharged and bubbling ceased, and then the mixture was evaporated. The material was purified twice by flash chromatography (EtOAc to 5% MeOH in EtOAc) to provide the methyl ester of Formula 302, 2-amino-4-tert-butoxycarbonylamino-butyric acid methyl ester, as a pale yellow wax (1.4 g, 58%).

5B. Formula 303 where $R^6$, $R^7$, $R^8$ and $R^9$ are H: and $R^{10}$ is p-Methyl-benzyl:

To a solution of 2-amino-4-tert-butoxycarbonylamino-butyric acid methyl ester (0.60 g, 2.58 mmol) in 100 mL of DCM was added p-tolualdehyde (282 µL, 2.39 mmol) and the mixture stirred at room temperature for 1 hour. Sodium triacetoxyborohydride (820 mg, 3.87 mmol) was added and the mixture stirred overnight. The solution was then washed with water and dried over magnesium sulfate. The solvents were evaporated and the residue dissolved in 100 mL of 2M HCl in dioxane solution and stirred for 2 hours. The solvent was evaporated and the residue dried under vacuum to give the desired compound of Formula 303, 4-amino-2-(4-methyl-benzylamino)-butyric acid methyl ester as its HCl salt (475 mg, 62%). This was taken on without further purification.

5C. Formula 304 where $R^6$, $R^7$, $R^8$ and $R^9$ are H; and $R^{10}$ is p-Methyl-benzyl:

To a solution of 4-amino-2-(4-methyl-benzylamino)-butyric acid methyl ester HCl salt (923 mg, 3.13 mmol) and DIEA (1.08 mL, 6.26 mmol) in 100 mL of DCM was added carbonyldiimidazole (760 mg, 4.69 mmol). The reaction mixture was stirred for 1 hour, after which the solvents were evaporated. The residue was dissolved in 20 mL of MeOH:$H_2O$ (2:1) solution to which was added LiOH (150 mg, 6.26 mmol). The mixture was stirred at room temperature for 3 hours and then adjusted to pH ~7 by adding Dowex-H+ resin. The solution was filtered, the solvent was evaporated, and the residue dried under vacuum to give the desired compound of Formula 304, 3-(4-methyl-benzyl)-2-oxo-hexahydro-pyrimidine-4-carboxylic acid (520 mg, 67%), which was taken on without further purification.

5D. Formula 402 where $R^1$, $R^2$, $R^4$, $R^6$, $R^7$, $R^8$ and $R^9$ are H; $R^3$ is Chloro; $R^5$ is Benzyl; $R^{10}$ is p-Methyl-benzyl; and V is N—R''' where R''' is H: To a solution of 3-(4-methyl-benzyl)-2-oxo-hexahydro-pyrimidine-4-carboxylic acid (400 mg, 1.61 mmol) in 20 mL of DMF was added anhydrous N-methylmorpholine (212 µL, 1.93 mmol). After cooling in an ice-bath for 10 min, isobutyl chloroformate (251 µL, 1.93 mmol) was added dropwise at while maintaining the temperature below 5° C. The mixture was stirred in the ice-bath for 1 hour, and 4-chloroanthranilic acid (331 mg, 1.93 mmol) in 1 mL of DMF was added. The mixture was stirred an additional 5 h during which the temperature was allowed to warm to room temperature to afford the corresponding intermediate product of Formula 305, which was carried on without isolation or purification. EDC (618 mg, 3.22 mmol) was then added into the reaction, the mixture was stirred for 1 hour, and benzylamine (528 µL, 4.83 mmol) was added. The resulting solution was stirred overnight, after which the solvents were evaporated and the residue purified by flash silica gel chromatography (stepwise gradient 1:4, 1:2, 1:1, 2:1, 4:1 with ethyl acetate:hexanes as eluent) to give the pure bis-amide product of Formula 402, 3-(4-methyl-benzyl)-2-oxo-hexahydro-pyrimidine-4-carboxylic acid (2-benzylcarbamoyl-5-chloro-phenyl)-amide (430 mg, 54%).

5E. Formula I where $R^1$, $R^2$, $R^4$, $R^6$, $R^7$, $R^8$ and $R^9$ are H, $R^3$ is Chloro; $R^5$ is Benzyl; $R^{10}$ is p-Methyl-benzyl; and V is N—R''' where R''' is H: 3-(4-Methyl-benzyl)-2-oxo-hexahydro-pyrimidine-4-carboxylic acid (2-benzylcarbamoyl-5-chloro-phenyl)-amide (350 mg, 0.713 mmol) was dissolved in 60 mL of ethylene glycol to which was added sodium hydroxide (60 mg, 1.5 mmol). The mixture was stirred at 140° C. for 20 hours and monitored by LC-MS. Following consumption of starting material, the reaction mixture was poured into 100 mL of water. After extraction with DCM, the crude product was purified by flash silica gel chromatography (stepwise gradient 1:4, 1:2, 1:1, 2:1, 4:1 with ethyl acetate:hexanes as eluent) to give the desired product of Formula I, 3-benzyl-7-chloro-2-[3-(4-methyl-benzyl)-2-oxo-hexahydro-pyrimidin-4-yl]-3H-quinazolin-4-one (180 mg, 53%).

Example 6

Compounds of Formula II where $R^6$ to $R^9$ are H; $R^5$ is Benzyl; $R^{10}$ is p-Methyl-benzyl; T is Methylene and V is N—R''' where R''' is H, Varying R' to $R^4$ and W, X, Y and Z By following the procedure as described in Example 5 and substituting 4-chloroanthranilic acid with the following:
3-amino-pyrazine-2-carboxylic acid;
3-amino-1,4-dihydro-pyridine-2-carboxylic acid;
2-amino-cyclopent-1-enecarboxylic acid;
4-amino-2,5-dihydro-furan-3-carboxylic acid; and
3-amino-1H-pyrrole-2-carboxylic acid, there are obtained the following respective compounds:
3-benzyl-2-[3-(4-methyl-benzyl)-2-oxo-hexahydro-pyrimidin-4-yl]-3H-pteridin-4-one;
3-benzyl-2-[3-(4-methyl-benzyl)-2-oxo-hexahydro-pyrimidin-4-yl]-5,8-dihydro-3H-pyrido[3,2-d]pyrimidin-4-one;
3-benzyl-2-[3-(4-methyl-benzyl)-2-oxo-hexahydro-pyrimidin-4-yl]-3,5,6,7-tetrahydro-cyclopentapyrimidin-4-one;
  3-benzyl-2-[3-(4-methyl-benzyl)-2-oxo-hexahydro-pyrimidin-4-yl]-5,7-dihydro-3H-furo[3,4-d]pyrimidin-4-one; and
3-benzyl-2-[3-(4-methyl-benzyl)-2-oxo-hexahydro-pyrimidin-4-yl]-3,7-dihydro-pyrrolo[3,2-d]pyrimidin-4-one.

Example 7

Induction of Mitotic Arrest in Cell Populations Treated with a KSP Inhibitor

FACS analysis to determine cell cycle stage by measuring DNA content is performed as follows. Skov-3 cells (human ovarian cancer) are split 1:10 for plating in 10 cm dishes and grown to subconfluence with RPMI 1640 medium containing 5% fetal bovine serum (FBS). The cells are then treated with either 10 nM paclitaxel, 400 nM test compound, 200 nM test compound, or 0.25% DMSO (vehicle for compounds) for 24 hours. A well known anti-mitotic agent, such as placitaxel, is used as a positive control. Cells are then rinsed off the plates with PBS containing 5 mM EDTA, pelleted, washed once in PBS containing 1% FCS, and then fixed overnight in 85% ethanol at 4° C. Before analysis, the cells are pelleted, washed once, and stained in a solution of 10 μg propidium iodide and 250 μg of ribonuclease (RNAse) A per milliliter at 37° C. for half an hour. Flow cytometry analysis is performed on a Becton-Dickinson FACScan, and data from 10,000 cells per sample is analyzed with Modfit software.

Monopolar Spindle Formation following Application of a Quinazolinone KSP Inhibitor To determine the nature of G2/M accumulation, human tumor cell lines Skov-3 (ovarian), HeLa (cervical), and A549 (lung) are plated in 96-well plates at densities of 4,000 cells per well (SKOV-3 & HeLa) or 8,000 cells per well (A549), allowed to adhere for 24 hours, and treated with various concentrations of the test compounds for 24 hours. Cells are fixed in 4% formaldehyde and stained with anti-tubulin antibodies (subsequently recognized using fluorescently-labeled secondary antibody) and Hoechst dye (which stains DNA). The cells can be visually inspected to assess the effects of the test compounds. For example, microinjection of anti-KSP antibodies causes mitotic arrest with arrested cells displaying monopolar spindles.

Example 8

Inhibition of Cellular Proliferation in Tumor Cell Lines Treated with KSP Inhibitors Cells are plated in 96-well plates at densities from 1000–2500 cells/well (depending on the cell line) and allowed to adhere/grow for 24 hours. They are then treated with various concentrations of test compound for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96® AQ$_{ueous}$ One Solution Cell Proliferation Assay) is used to determine the number of viable cells at $T_0$ and the number of cells remaining after 48 hours compound exposure. The number of cells remaining after 48 hours is compared to the number of viable cells at the time of test compound addition, allowing for calculation of growth inhibition. The growth over 48 hours of cells in control wells treated with vehicle only (0.25% DMSO) is considered 100% growth and the growth of cells in wells with compounds is compared to this. Active KSP inhibitors inhibit cell proliferation in one or more human tumor cell lines of the following tumor types: lung (NCI-H460, A549), breast (MDA-MB-231, MCF-7, MCF-7/ADR-RES), colon (HT29, HCT15), ovarian (SKOV-3, OVCAR-3), leukemia (HL-60(TB), K-562), central nervous system (SF-268), renal (A498), osteosarcoma (U2-OS), and cervical (HeLa), and mouse tumor line (B16, melanoma).

Calculation Of $GI_{50}$: A $GI_{50}$ is calculated by plotting the concentration of compound in μM vs the percentage of cell growth of cell growth in treated wells. The $GI_{50}$ calculated for the compounds is the estimated concentration at which growth is inhibited by 50% compared to control, i.e., the concentration at which:

$$100 \times [(\text{Treated}_{48} - T_0)/(\text{Control}_{48} - T_0)] = 50.$$

All concentrations of compounds are tested in duplicate and controls are averaged over 12 wells. A very similar 96-well plate layout and $GI_{50}$ calculation scheme is used by the National Cancer Institute (see Monks, et al., J. Natl. Cancer Inst. 83:757–766 (1991)). However, the method by which the National Cancer Institute quantitates cell number does not use MTS, but instead employs alternative methods.

Calculation Of $IC_{50}$: Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM MgC12 (VWR JT400301), and 1 mM EGTA (Sigma E3889). Solution 2 consists of 1 mM NADH (Sigma N8129), 0.2 mg/ml BSA (Sigma A7906), pyruvate kinase 7U/ml, L-lactate dehydrogenase 10 U/ml (Sigma P0294), 100 nM KSP motor domain, 50 μg/ml microtubules, 1 mM DTT (Sigma D9779), 5 μM paclitaxel (Sigma T-7402), 10 ppm antifoam 289 (Sigma A-8436), 25 mM Pipes/KOH pH 6.8 (Sigma P6757), 2 mM MgC12 (VWR JT4003-01), and 1 mM EGTA (Sigma E3889). Serial dilutions (8–12 two-fold dilutions) of the composition are made in a 96-well microtiter plate (Corning Costar 3695) using Solution 1. Following serial dilution each well has 50 µl of Solution 1. The reaction is started by adding 50 µl of Solution 2 to each well. This can be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{Range}{1 + \left(\frac{x}{IC_{50}}\right)^s} + Background$$

where y is the observed rate and x the compound concentration.

Example 9

Inhibition of Cellular Viability in Tumor Cell Lines Treated with KSP Inhibitors Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.
Procedure: Day 1—Cell Plating: Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C., 100% humidity, and 5% $CO_2$, allowing the cells to adhere to the plates.
Procedure: Day 2—Compound Addition: To one column of the wells of an autoclaved assay block are added an initial 2.5 µL of test compound(s) at 400× the highest desired concentration. 1.25 µL of 400× (400 µM) Topotecan is added to other wells (ODs from these wells are used to subtract out for background absorbance of dead cells and vehicle). 500 µL of media without DMSO are added to the wells containing test compound, and 250 µL to the Topotecan wells. 250 µL of media+0.5% DMSO is added to all remaining wells, into which the test compound(s) are serially diluted. By row, compound-containing media is replica plated (in duplicate) from the assay block to the corresponding cell plates. The cell plates are incubated for 72hours at 37° C., 100% humidity, and 5% $CO_2$.
Procedure: Day 4—MTS Addition and OD Reading: The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis The normalized % of control (absorbance-background) is calculated and an XLfit is used to generate a dose-response curve from which the concentration of compound required to inhibit viability by 50% is determined.

The compounds of the present invention show activity when tested in one or more of the methods described in Examples 7, 8 and 9.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound selected from the group represented by Formula I:

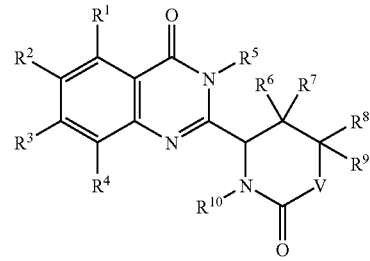

Formula I where:
V is a covalent bond, CR'R" or NR'",
    R' and R" being independently hydrogen, hydroxy, amino, aryl, substituted aryl, alkylamino, substituted alkylamino, alkyl, substituted alkyl, alkoxy, or substituted alkoxy, and
    R'" being hydrogen, alkyl, substituted alkyl, aryl, substituted aryl, aralkyl, substituted aralkyl, heteroaryl, substituted heteroaryl, heteroaralkyl, or substituted heteroaralkyl;
$R^1$, $R^2$, $R^3$ and $R^4$ are independently hydrogen, hydroxy, alkyl, substituted alkyl, alkoxy, substituted alkoxy, halogen or cyano;
$R^5$ is hydrogen, alkyl, substituted alkyl, aryl, substituted aryl, aralkyl, substituted aralkyl, heteroaryl, substituted heteroaryl, heteroaralkyl, or substituted heteroaralkyl;
$R^6$ to $R^9$ are independently hydrogen, hydroxy, alkyl, substituted alkyl, alkoxy, substituted alkoxy, aryl, substituted aryl, alkylamino, or substituted alkylamino, provided that neither $R^8$ nor $R^9$ is hydroxy or alkoxy when V is NR'"; and
$R^{10}$ is hydrogen, alkyl, substituted alkyl, aryl, substituted aryl, aralkyl, substituted aralkyl, heteroaryl, substituted heteroaryl, heteroaralkyl, or substituted heteroaralkyl,
or a pharmaceutically acceptable salt thereof, wherein "substituted" as used with regard to alkyl, aryl, aralkyl, heteroaryl and heterocyclyl refers to an alkyl, aryl, aralkyl, heteroaryl or heterocyclyl moiety, respectively, wherein one or more hydrogen atoms are replaced by a substituent independently selected from the group: acyl, acyloxy, alkyl, alkoxy, amino, alkylamino, dialkylamino, carbonylamino, benzyloxycarbonylamino, carboxamido, amidino, aryl, aralkyl, aryloxy, aralkoxy, heteroaryl, heteroaralkyl, heteroaryloxy, heteroaralkoxy, carboxy (—COOH), cyano, halogen, hydroxy, nitro, sulfanyl, sulfinyl, and sulfonyl.

2. The compound of claim 1 comprising one or more of the following:
V is $CH_2$, or $NR'''$;
$R^1$, $R^2$, $R^3$ and $R^4$ are independently hydrogen, halo, lower alkyl, substituted lower alkyl, lower alkoxy or cyano;
$R^5$ is aralkyl or substituted aralkyl;
$R^6$ to $R^9$ are independently hydrogen, lower alkyl, or substituted lower alkyl;
and $R^{10}$ is benzyl, substituted benzyl, phenyl, or substituted phenyl.

3. The compound of claim 2 comprising one or more of the following:
$R^1$, $R^2$, $R^3$ and $R^4$ are independently hydrogen, chloro, fluoro, methyl, methoxy or cyano;
$R^5$ is benzyl or substituted benzyl;
$R^6$ to $R^9$ are hydrogen; and
$R^{10}$ is benzyl or p-methyl-benzyl.

4. The compound of claim 3 where $R^1$, $R^2$, $R^3$ and $R^4$ are hydrogen, or three of $R^1$, $R^2$, $R^3$ and $R^4$ are hydrogen and the fourth is halo, methoxy, methyl or cyano.

5. The compound of claim 4 where V is —NH—, —N(alkyl)-, or —N(substituted alkyl)-.

6. A compound selected from:
3-benzyl-7-chloro-2-[3-benzyl-2-oxo-hexahydro-pyrimidin-4-yl]-3H-quinazolin-4-one;
3-benzyl-7-chloro-2-[3-(4-methyl-1-benzyl)-2-oxo-hexahydro-pyrimidin-4-yl]-3H-quinazolin-4-one;
3-benzyl-2-(1-benzyl-6-oxo-piperidin-2-yl)-7-chloro-3H-quinazolin-4-one;
3-benzyl-2-(1(4-methyl-benzyl)-6-oxo-piperidin-2-yl)-7-chloro-3H-quinazolin-4-one; and
2-[-1-(2-amino-ethyl)-3-(4-methyl-benzyl)-2-oxo-hexahydro-pyrimidin-4-yl]-3-benzyl-7-chloro-3H-quinazolin-4-one,
or a pharmaceutically acceptable salt thereof.

7. A compound selected from:
3-benzyl-7-chloro-2-[3-(4-methyl-1-1-benzyl)-2oxo-hexahydro-pyrimidin-4-yl]-3H-quinazolin-4-one;
3-benzyl-2-(1-benzyl-6-oxo-piperidin-2-yl)-7-chloro-3H-quinazolin-4-one; and
3-benzyl-2-(1-(4-methyl-benzyl)-6-oxo-piperidin-2-yl)-7-chloro-3H-quinazolin-4-one, or a pharmaceutically acceptable salt thereof.

8. A pharmaceutical formulation comprising a pharmaceutically acceptable excipient and an effective amount of a compound of any of claims 1 to 5, 6, or 7.

9. A kit comprising a compound of any of claims 1 to 5, 6, or 7.

* * * * *